United States Patent
Kuo et al.

(10) Patent No.: US 9,023,867 B2
(45) Date of Patent: May 5, 2015

(54) HYDROPHILIC DERIVATIVES OF 2-SELENOPHENE-4-QUINOLONES AS ANTICANCER AGENTS

(71) Applicant: China Medical University, Taichung (TW)

(72) Inventors: Sheng-Chu Kuo, Taichung (TW); Che-Ming Teng, Taipei (TW); Kuo-Hsiung Lee, Chapel Hill, NC (US); Li-Jiau Huang, Taichung (TW); Li-Chen Chou, Taichung (TW); Chih-Shiang Chang, Taichung (TW); Chung-Ming Sun, Hsinchu (TW); Tian-Shung Wu, Tainan (TW); Shiow-Lin Pan, Taipei (TW); Tzong-Der Way, Taichung (TW); Jang-Chang Lee, Taichung (TW); Jing-Gung Chung, Taichung (TW); Jai-Sing Yang, Taichung (TW); Chien-Ting Chen, Taichung (TW); Ching-Che Huang, Taichung (TW); Shih-Ming Huang, Taichung (TW)

(73) Assignee: China Medical University, Taichung (TW)

( * ) Notice: Subject to any disclaimer, the term of this patent is extended or adjusted under 35 U.S.C. 154(b) by 37 days.

(21) Appl. No.: 13/892,576

(22) Filed: May 13, 2013

(65) Prior Publication Data

US 2013/0244983 A1 Sep. 19, 2013

Related U.S. Application Data

(62) Division of application No. 12/448,088, filed as application No. PCT/US2007/025056 on Dec. 7, 2007, now Pat. No. 8,440,692.

(60) Provisional application No. 60/873,258, filed on Dec. 7, 2006.

(51) Int. Cl.
| C07D 421/04 | (2006.01) |
| C07F 9/6561 | (2006.01) |
| C07F 9/60 | (2006.01) |
| C07D 215/233 | (2006.01) |
| C07D 491/056 | (2006.01) |

(52) U.S. Cl.
CPC ............ *C07F 9/6561* (2013.01); *C07D 421/04* (2013.01); *C07F 9/60* (2013.01); *C07D 215/233* (2013.01); *C07D 491/056* (2013.01)

(58) Field of Classification Search
CPC ..................................................... C07D 421/04
See application file for complete search history.

(56) References Cited

U.S. PATENT DOCUMENTS

| 5,571,822 A | 11/1996 | Lee et al. |
| 6,894,039 B2 | 5/2005 | Chang et al. |
| 6,897,316 B2 | 5/2005 | Kuo et al. |
| 7,078,552 B2 | 7/2006 | Pettit et al. |

OTHER PUBLICATIONS

Heimbach et al. International Journal of Pharmaceutics, 2003, vol. 261, pp. 81-92.*

* cited by examiner

*Primary Examiner* — James D Anderson
(74) *Attorney, Agent, or Firm* — Bacon & Thomas, PLLC

(57) ABSTRACT

2-aryl-4-quinolones are converted into phosphates by reacting with tetrabenzyl pyrophosphate to form dibenzyl phosphates thereof, which are then subject to hydrogenation to replace dibenzyl groups with H, followed by reacting with Amberlite IR-120 ($Na^+$ form) to form disodium salts. The results of preliminary screening revealed that these phosphates showed significant anti-cancer activity. A novel intermediate, 2-selenophene 4-quinolone and N,N-dialkylaminoalkyl derivatives of 2-phenyl-4-quinolones are also synthesized. These novel intermediates exhibited significant anticancer activities.

5 Claims, 3 Drawing Sheets

HYDROPHILIC DERIVATIVES OF 2-SELENOPHENE-4-QUINOLONES AS ANTICANCER AGENTS

FIELD OF THE INVENTION

The present invention relates to novel phosphate derivatives of 2-aryl-4-quinolones, and novel intermediates, 2-selenophene 4-quinolones and N,N-dialkylaminoalkyl derivatives of 2-phenyl-4-quinolones; and in particular to their uses in treating human cancers.

BACKGROUND OF THE INVENTION

Quinolone derivatives were initially discovered as the agents to act on bacterial DNA gyrase, and thus developed as anti-bacterial agents. Recently DNA topoisomerase II has emerged as the pharmacological target for this class of quinolone compounds. We have synthesized a series of substituted 2-phenyl-4-quinolone (A) which appeared to function as novel antimitotic agents. [Kuo, S. C., Lee, H. Z., Juang, J. P., Lin, Y. T., Wu, T. S., Chang, J. J., Lednicer, D., Paull, K. D., Lin, C. M., Hamel, E. Synthesis and cytotoxicity of 1,6,7,8-substituted 2-(4'-substituted phenyl)-4-quinolones and related compounds: identification as antimitotic agents interacting with tubulin. *J. Med. Chem.* 1993, 36, 1146-56; Li, L., Wang, H. K., Kuo, S. C., Wu, T. S., Mauger, A., Lin. C. M., Hamel, E. Lee, K. H. Antitumor agents. 155. Synthesis and biological evaluation of 3',6,7-substituted 2-phenyl-4-quinolones as antimicrotubule agents. *J. Med. Chem.* 1994, 37, 3400-7] Later on we continued to synthesize many related analogs such as 2-phenylnaphthyridine-4-ones (B) [Chen, K., Kuo, S. C., Hsieh, M. C., Mauger, S A., Lin, C. M., Hamel, E., Lee, K. H. Antitumor agents. 174. 2',3',4',5,6,7-Substituted 2-phenyl-1,8-naphthyridin-4-ones: their synthesis, cytotoxicity, and inhibition of tubulin polymerization. *J. Med. Chem.* 1997, 40, 2266-75], 2-phenyl-4-quinazolones (C) [Xia, Y., Yang, Z. Y., Hour, M. J., Kuo, S. C., Xia, P., Bastow, K. F., Nakanishi, Y, Namrpoothiri, P., Hackl, T., Hamel, E., Lee, K. H. Antitumor Agents. Part 204: Synthesis and Biological Evaluation of Substituted 2-Aryl Quinazolinones, *Bioorg. Med. Chem. Lett.* 2001, 11, 1193-6; Hour, M. J., Huang, L. J., Kuo, S. C., Xia, Y., Bastow, K. F., Nakanishi, Y., Hamel, E., Lee, K. H. 6-Alkylamino- and 2,3-dihydro-3'-methoxy-2-phenyl-4-quinazolinones and related compounds: their synthesis, cytotoxicity, and inhibition of tubulin polymerization. *J. Med. Chem.* 2000, 43, 4479-87] and tetrahydro-2-phenyl-4-quinolones (D) [Xia, Y., Yang, Z. Y., Xia, P., Bastow, K. F., Tachibana, Y., Kuo, S. C., Hamel, E., Hackl. T., Lee, K. H. Antitumor agents. 181. Synthesis and biological evaluation of 6,7,2',3',4'-substituted-1,2,3,4-tetrahydro-2-phenyl-4-quinolones as a new class of antimitotic antitumor agents. *J. Med. Chem.* 1998, 41. 1155-62], which enable us to establish structure and activity relationships (SAR). Among these analogs, we have discovered quite a few compounds possessing potent cytotoxicity, such as 3',6-disubstituted 2-phenyl-4-quinolones (A-1) etc [Li, L., Wang, H. K., Kuo, S. C., Wu, T. S., Lednicer, D., Lin, C. M., Hamel, E., Lee, K. H. Antitumor agents. 150. 2',3',4',5',5,6,7-substituted 2-phenyl-4-quinolones and related compounds: their synthesis, cytotoxicity, and inhibition of tubulin polymerization. *J. Med. Chem.* 1994, 37, 1126-35]. However, most of the compounds with potent cytotoxicity were very lipophilic, and therefore, not suitable for in vivo and clinical studies. We thus made attempt to synthesize hydrophilic derivatives of these 2-aryl-4-quinolone skeletons in order to improve pharmacokinetic properties suitable for in vivo and clinical studies.

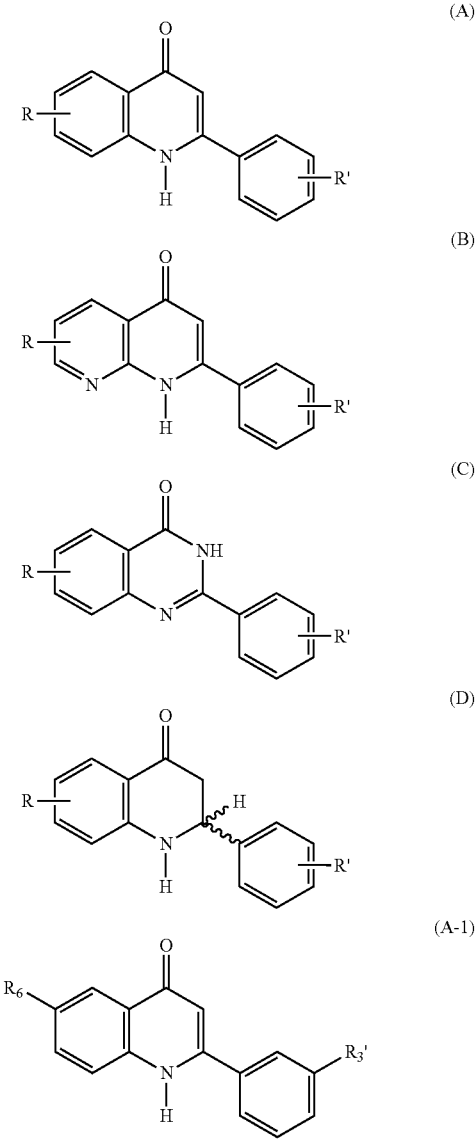

SUMMARY OF THE INVENTION

Preferred embodiments of the present invention include (but not limited thereto) the following items:

1. A phosphate derivative of 2-aryl-4-quinolone having the following formulas Ia, Ib or Ic:

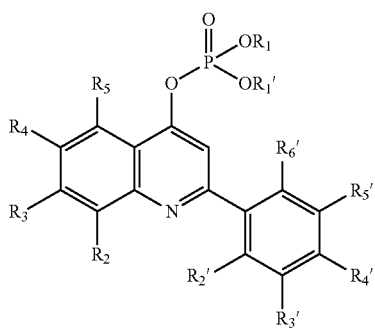

Ia

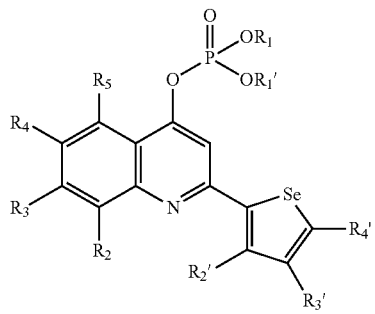

Ib

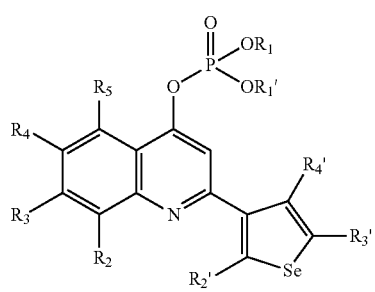

Ic wherein $R_2'$, $R_3'$, $R_4'$, $R_5'$ and $R_6'$ independently are H, $(CH_2)_nCH_3$, $(CH_2)_nYH$, $Y(CH_2)_nCH_3$, $Y(CH_2)_nYH$, $Y(CH_2)_nNR_8R_9$, X, $(CH_2)_nNR_8R_9$,

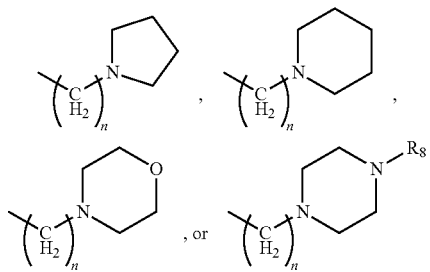

wherein n is an integer of 0-4, Y is O or S, X is F, Cl, or Br, and $R_8$ and $R_9$ independently are H, $(CH_2)_nYH$, $(CH_2)_nN(C_nH_{2n+1})(C_mH_{2m+1})$ or $(CH_2)_nCH_3$, wherein n and Y are defined as above, and m is an integer of 0-4;

$R_2$, $R_3$, $R_4$ and $R_5$ independently are H, $(CH_2)_nCH_3$, $(CH_2)_nYH$, $Y(CH_2)_nCH_3$, $Y(CH_2)_nYH$, $Y(CH_2)_nNR_8R_9$, X, $(CH_2)_nNR_8R_9$,

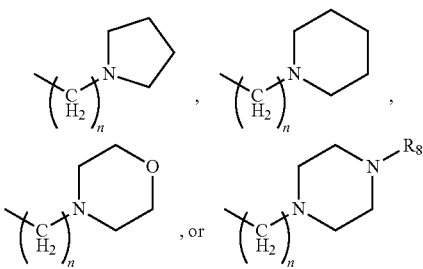

or $R_3$ and $R_4$ together is —$Y(CH_2)_nY$—, wherein n, Y, X, $R_8$ and $R_9$ are defined as above; and $R_1$ and $R_1'$ independently are H, Li$^+$, Na$^+$, K$^+$, N$^+R_8R_9R_{10}R_{11}$ or benzyl wherein $R_{10}$ and $R_{11}$ independently are H, $(CH_2)_nYH$, $(CH_2)_nN(C_nH_{2m+1})(C_mH_{2m+1})$ or $(CH_2)_nCH_3$, n, m, $R_8$ and $R_9$ are defined as above.

2. The phosphate derivative according to Item 1, which has the formula Ia.

3. The phosphate derivative according to Item 2, wherein $R_2'$, $R_3'$, $R_4'$, $R_5'$ and $R_6'$ are all H; or one of $R_2'$, $R_3'$, $R_4'$, $R_5'$ and $R_6'$ is F, OCH$_3$ or $(CH_2)_nNR_8R_9$, and the others thereof are H, wherein n, $R_8$ and $R_9$ are defined as in Item 1.

4. The phosphate derivative according to Item 2, wherein $R_2$, $R_3$, $R_4$, and $R_5$ are all H; or one of $R_2$, $R_3$, $R_4$, and $R_5$ is F, OCH$_3$, $Y(CH_2)_nCH_3$ or $(CH_2)_nNR_8R_9$, and the others thereof are H; or $R_2$ and $R_5$ are H, and $R_3$ and $R_4$ together is —O(CH$_2$)$_n$O—, wherein n, Y, $R_8$ and $R_9$ are defined as in Item 1.

5. The phosphate derivative according to Item 2, wherein $R_1$ and $R_1'$ are both H or both Na$^+$.

6. The phosphate derivative according to Item 5, wherein $R_2$ and $R_5$ are H, and $R_3$ and $R_4$ together is —O(CH$_2$)O—; and $R_2'$, $R_3'$, $R_4'$ and $R_5'$ are all H, and $R_6'$ is F.

7. The phosphate derivative according to Item 5, wherein $R_2$ and $R_5$ are H, and $R_3$ and $R_4$ together is —O(CH$_2$)O—; and $R_2'$, $R_3'$, $R_4'$ and $R_6'$ are all H, and $R_5'$ is F.

8. The phosphate derivative according to Item 5, wherein $R_4$ is F, and $R_2$, $R_3$ and $R_5$ are H; and $R_2'$, $R_3'$, $R_4'$, $R_5'$ and $R_6'$ are all H.

9. The phosphate derivative according to Item 5, wherein $R_2$, $R_3$, $R_4$ and $R_5$ are all H; and $R_2'$, $R_3'$, $R_4'$, $R_5'$ and $R_6'$ are all H.

10. The phosphate derivative according to Item 5, wherein $R_4$ is OCH$_3$, and $R_2$, $R_3$ and $R_5$ are H; and $R_5'$ is F, and $R_2'$, $R_3'$, $R_4'$ and $R_6'$ are H.

11. The phosphate derivative according to Item 5, wherein $R_2$ and $R_5$ are H, and $R_3$ and $R_4$ together is —O(CH$_2$)O—; and $R_2'$, $R_3'$, $R_4'$ and $R_6'$ are all H, and $R_5'$ is OCH$_3$.

12. The phosphate derivative according to Item 5, wherein $R_4$ is CH$_2$N(C$_2$H$_5$)$_2$, and $R_2$, $R_3$ and $R_5$ are H; and $R_6'$ is F, and $R_2'$, $R_3'$, $R_4'$ and $R_5'$ are H.

13. The phosphate derivative according to Item 5, wherein $R_4$ is CH$_2$N(C$_2$H$_5$)$_2$, and $R_2$, $R_3$ and $R_5$ are H; and $R_2'$, $R_3'$, $R_4'$, $R_5'$ and $R_6'$ are all H.

14. The phosphate derivative according to Item 5, wherein $R_4$ is OCH$_3$, and $R_2$, $R_3$ and $R_5$ are H; and $R_5'$ is CH$_2$N(C$_2$H$_5$)$_2$, and $R_2'$, $R_3'$, $R_4'$ and $R_6'$ are H.

15. The phosphate derivative according to Item 1, which has the formula Ib.

16. The phosphate derivative according to Item 15, wherein $R_2$, $R_3$, $R_4$, and $R_5$ are all H; or one of $R_2$, $R_3$, $R_4$ and $R_5$ is F or OCH$_3$, and the others thereof are H; or $R_2$ and $R_5$ are H, and $R_3$ and $R_4$ together is —O(CH$_2$)$_n$O—, wherein n is defined as in Item 1.

17. The phosphate derivative according to Item 15, wherein $R_2'$, $R_3'$ and $R_4'$ are all H; or one of $R_2'$, $R_3'$ and $R_4'$ is F or $OCH_3$, and the others thereof are H.

18. The phosphate derivative according to Item 15, wherein $R_1$ and $R_1'$ are benzyl.

19. The phosphate derivative according to Item 18, wherein $R_2'$, $R_3'$, $R_4'$, $R_2$ and $R_5$ are all H, and $R_3$ and $R_4$ together is $-O(CH_2)O-$.

20. A pharmaceutical composition for the killing of solid cancer cells, which comprises a therapeutically effective amount of a phosphate derivative of 2-aryl-4-quinolone as set forth in any one of Item 1 to Item 19 or a pharmaceutically acceptable salt thereof, as an active ingredient, in admixture with a pharmaceutically acceptable carrier or diluent for the active ingredient, wherein the solid cancer cells comprise human breast cancer, colon cancer, lung cancer, melanoma, ovarian cancer, renal cancer, stomach cancer, prostate cancer, ileocecal carcinoma, glioblastoma, bone cancer, epidermoid carcinoma of the nasopharynx, hepatoma or leukemia cancer.

21. The pharmaceutical composition according to Item 20, wherein the solid cancer cells are human breast cancer, colon cancer, lung cancer, renal cancer, hepatoma, or leukemia cancer 22. The pharmaceutical composition according to Item 21, wherein the solid cancer cells are human breast cancer or colon cancer.

23. A compound of 2-selenophene 4-quinolone having the following formulas IIb or IIc:

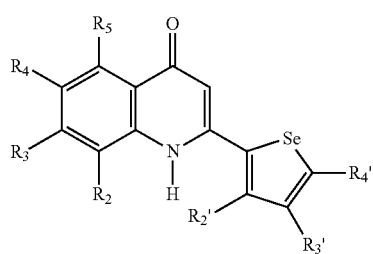

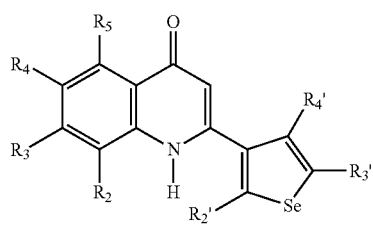

wherein $R_2'$, $R_3'$ and $R_4'$ independently are H, $(CH_2)_nCH_3$, $(CH_2)_nYH$, $Y(CH_2)_nCH_3$, $Y(CH_2)_nYH$, $Y(CH_2)_nNR_8R_9$, X, or $(CH_2)_nNR_8R_9$, wherein n is an integer of 0-4, Y is O or S, X is F, Cl, or Br, and $R_5$ and $R_9$ independently are H, $(CH_2)_nYH$, $(CH_2)_nN(C_nH_{2n+1})(C_mH_{2m+1})$ or $(CH_2)_nCH_3$, wherein n and Y are defined as above, and m is an integer of 0-4;

$R_2$, $R_3$, $R_4$ and $R_5$ independently are H, $(CH_2)_nCH_3$, $(CH_2)_nYH$, $Y(CH_2)_nCH_3$, $Y(CH_2)_nYH$, $Y(CH_2)_nNR_8R_9$, X, $(CH2)_nNR_8R_9$,

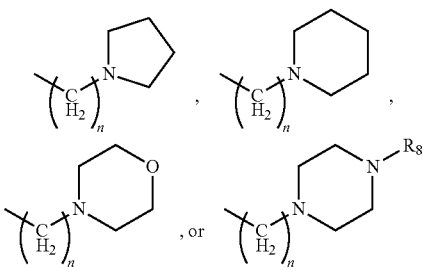

or $R_3$ and $R_4$ together is $-Y(CH_2)_nY-$, wherein n, Y, X, $R_8$ and $R_9$ are defined as above.

24. The compound according to Item 23, wherein $R_2$, $R_3$, $R_4$, and $R_5$ are all H; or one of $R_2$, $R_3$, $R_4$ and $R_5$ is F or $OCH_3$, and the others thereof are H; or $R_2$ and $R_5$ are H, and $R_3$ and $R_4$ together is $-O(CH_2)_nO-$, wherein n is defined as in Item 19.

25. The compound according to Item 24, wherein $R_2'$, $R_3'$ and $R_4'$ are all H; or one of $R_2'$, $R_3'$ and $R_4'$ is F or $OCH_3$, and the others thereof are H.

26. The compound according to Item 23 which has the formula IIb.

27. The compound according to Item 26, wherein $R_2'$, $R_3'$, $R_4'$, $R_2$ and $R_5$ are all H, and $R_3$ and $R_4$ together is $-O(CH_2)O-$.

28. A pharmaceutical composition for the killing of solid cancer cells, which comprises a therapeutically effective amount of a compound of 2-selenophene 4-quinolone as set forth in any one of item 23 to Item 27 or a pharmaceutically acceptable salt thereof, as an active ingredient, in admixture with a pharmaceutically acceptable carrier or diluent for the active ingredient, wherein the solid cancer cells comprise human breast cancer, colon cancer, lung cancer, melanoma, ovarian cancer, renal cancer, stomach cancer, prostate cancer, ileocecal carcinoma, glioblastoma, bone cancer, epidermoid carcinoma of the nasopharynx, hepatoma or leukemia cancer.

29. The pharmaceutical composition according to Item 28, wherein the solid cancer cells are human breast cancer, colon cancer, lung cancer, renal cancer, hepatoma, or leukemia cancer.

30. A compound of 2-phenyl-4-quinolone having the following formula IIa:

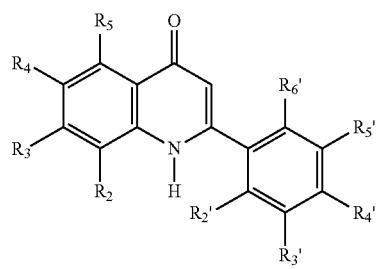

wherein $R_2'$, $R_3'$, $R_4'$, $R_5'$ and $R_6'$ independently are H, $(CH_2)_nCH_3$, $(CH_2)_nYH$, $Y(CH_2)_nCH_3$, $Y(CH_2)_nYH$, $Y(CH_2)_nNR_8R_9$, X, $(CH_2)_nNR_8R_9$,

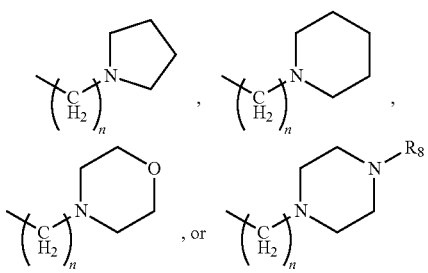

wherein n is an integer of 0-4, Y is O or S, X is F, Cl, or Br, and $R_8$ and $R_9$ independently are H, $(CH_2)_n YH$, $(CH_2)_n N(C_n H_{2n+1})(C_m H_{2m+1})$ or $(CH_2)_n CH_3$, wherein n and Y are defined as above, and m is an integer of 0-4;

$R_2$, $R_3$, $R_4$ and $R_5$ independently are H, $(CH_2)_n CH_3$, $(CH_2)_n YH$, $Y(CH_2)_n CH_3$, $Y(CH_2)_n YH$, $Y(CH_2)_n NR_3 R_9$, X, $(CH_2)_n NR_8 R_9$,

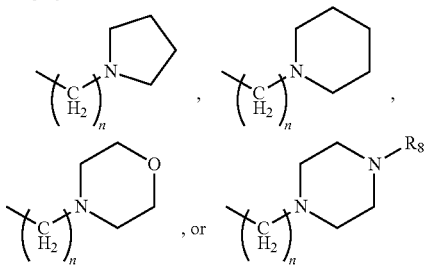

or $R_3$ and $R_4$ together is —$Y(CH_2)_n Y$—, wherein n, Y, X, $R_8$ and $R_9$ are defined as above;

provided that one of $R_2$, $R_3$, $R_4$ and $R_5$ is $(CH_2)_q NR_8 R_9$, or one of $R_2'$, $R_3'$, $R_4'$, $R_5'$ and $R_6'$ is $(CH_2)_q NR_8 R_9$, wherein q is an integer of 1-4, and $R_8$ and $R_9$ are defined as above.

31. The compound according to Item 30, wherein $R_4$ is $CH_2)_q NR_8 R_9$, and $R_2$, $R_3$ and $R_5$ are H, wherein q, $R_8$ and $R_9$ are defined as in Item 30.

32. The compound according to Item 30, wherein $R_5'$ is $CH_2)_q NR_8 R_9$, and $R_2'$, $R_3'$, $R_4'$ and $R_6'$ are H, wherein q, $R_8$ and $R_9$ are defined as in Item 30.

33. The compound according to Item 31, wherein $R_4$ is $CH_2 N(C_2 H_5)_2$, $R_6'$ is F, and $R_2'$, $R_3'$, $R_4'$ and $R_5'$ are H.

34. The compound according to Item 31, wherein $R_4$ is $CH_2 N(C_2 H_5)_2$, $R_2'$, $R_3'$, $R_4'$, $R_5'$ and $R_6'$ are all H.

35. The compound according to Item 32, wherein $R_4$ is $OCH_3$, and $R_2$, $R_3$ and $R_5$ are H; and $R_5'$ is $CH_2 N(C_2 H_5)_2$, and $R_2'$, $R_3'$, $R_4'$ and $R_6'$ are H.

36. A pharmaceutical composition for the killing of solid cancer cells, which comprises a therapeutically effective amount of a compound of 2-phenyl 4-quinolone as set forth in any one of Item 30 to Item 35 or a pharmaceutically acceptable salt thereof, as an active ingredient, in admixture with a pharmaceutically acceptable carrier or diluent for the active ingredient, wherein the solid cancer cells comprise human breast cancer, colon cancer, lung cancer, melanoma, ovarian cancer, renal cancer, stomach cancer, prostate cancer, ileocecal carcinoma, glioblastoma, bone cancer, epidermoid carcinoma of the nasopharynx, hepatoma or leukemia cancer.

37. The pharmaceutical composition according to Item 36, wherein the solid cancer cells are leukemia cancer.

DETAILED DESCRIPTION OF THE INVENTION

Figure 1:
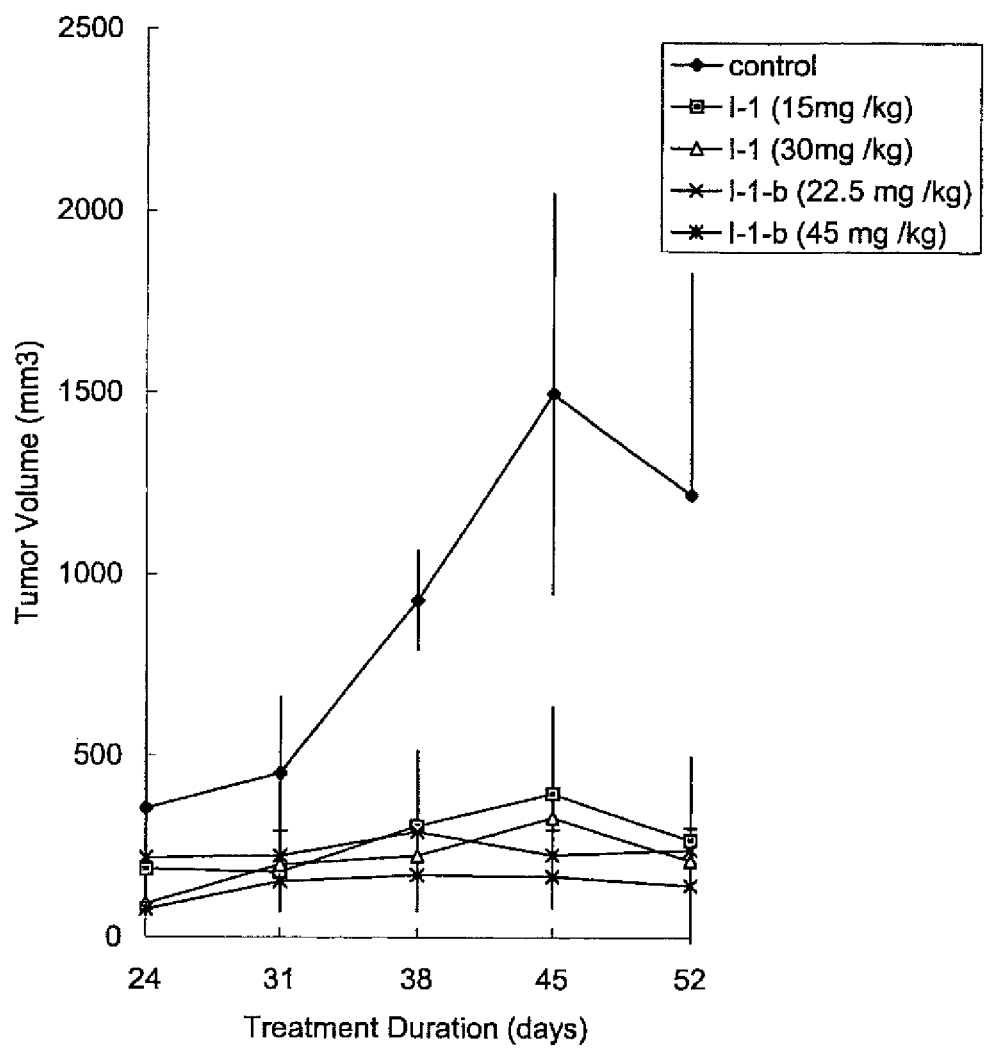
FIG. 1 shows effects of compound I-1 and compound I-1-b on MCF7 tumor growth in a mouse xenograft model. Female SCID mice received injections of MCF7 transfectants to induce tumor xenografts. Mice were divided into five groups. The second to fifth groups were given i.p. with compounds I-1 (15 mg/kg), I-1 (30 mg/kg), I-1-b (22.5 mg/kg), and I-1-b (45 mg/kg), respectively, three times per week. Data are expressed as mean of tumor weights (g)±S.E.M.*$p<0.05$ compared with the control.

As shown in the following Examples 1 to 6, when 2-phenyl-4-quinolones (I-1 to I-6) was reacted with tetrabenzyl pyrophosphate in the presence of alkali, the corresponding phosphoric acid dibenzyl esters (I-1-a to I-6-a) were obtained. Catalytic hydrogenation of compounds (I-1-a to I-6-a) in alcohol affords the corresponding phosphoric acid mono esters (I-1-b to I-6-b), which could be led to water soluble salts (I-1-c to I-6-c).

Example 1

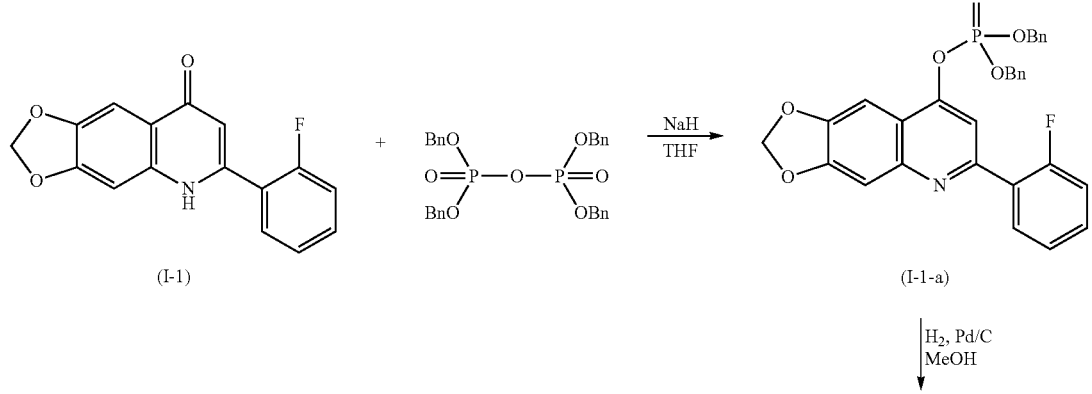

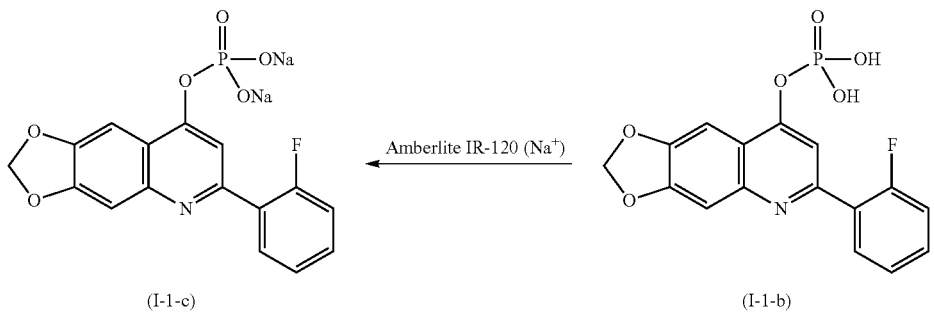

Dibenzyl 2-(2'-fluorophenyl)-6,7-methylenedioxyquinolin-4-yl-phosphate (I-1-a)

Sodium hydride (13.7 mg, 0.57 mmol) was added at 0° C. to a stirred solution of compound I-1 (64.5 mg, 0.23 mmol) in dry tetrahydrofuran (10 ml). After 1 h, tetrabenzyl pyrophosphate (100 mg, 0.19 mmol) was added and the stirring was continued for 20 min.

The mixture was filtered, and the filtrate was concentrated under vacuum at a temperature below 35° C. The residue was dissolved in dichloromethane, washed with an aqueous solution of sodium hydrogen carbonate, dried over MgSO$_4$ and concentrated under vacuum to give compound I-1-a (69.1 mg, 67%)

MP 101-104° C.

$^1$H-NMR (CDCl$_3$, 300 MHz): δ 8.01-8.02 (m, 1H, H-5'), 7.77 (s, 1H, H-5), 7.16-7.43 (m, 14H, H-3, H-3', H-4', H-6', Ph), 7.05 (s, 1H, H-8), 6.12 (s, 2H, OCH$_2$O), 5.26 (s, 2H, —CH$_2$-Ph), 5.20 (s, 2H, —CH$_2$-Ph)

MS (m/z) 544 (ES+)

Anal. calcd for C$_{30}$H$_{25}$FNO$_6$P: C, 66.30; H, 4.27; N, 2.58. Found: C, 66.28; H, 4.35; N, 2.55.

2-(2'-Fluorophenyl)-6,7-methylenedioxyquinolin-4-yl-phosphate (I-1-b)

A suspension of compound I-1-a (97.7 mg, 0.18 mmol) in anhydrous MeOH (10 ml) was submitted to hydrogenation in the presence of 10% Pd/C (50 mg) at room temperature for 10 min. The catalyst and precipitates was collected and dissolved in 10% NaHCO$_3$ solution then filtered. The filtrate was acidified with dil HCl, the solid was then collected by filtration and washed with acetone to give compound I-1-b (63.5 mg, 97.2%).

MP>300° C.

$^1$H-NMR (DMSO-d6, 300 MHz): δ 7.93-7.98 (m, 1H, H-5'), 7.74 (s, 1H, H-5), 7.49-7.54 (m, 1H, H-4'), 7.32-7.41 (m, 4H, H-3, H-8, H-3', H-6'), 6.22 (s, 2H, OCH$_2$O).

MS (m/z) 362 (ES−)

Anal. calcd for C$_{16}$H$_{13}$FNO$_6$P: C, 52.91; H, 3.05; N, 3.86. Found: C, 52.73; H, 3.10; N, 3.81.

Sodium 2-(2'-fluorophenyl)-6,7-methylenedioxyquinolin-4-yl-phosphate (I-1-c)

Compound I-1-b was added to a mixture of 20 ml Amberlite IR-120 (Na$^+$ form) and 20 ml water, and then stirred for 6 h at room temperature. The mixture was then filtered to remove Amberlite, and then lyophilized to give I-1-c (49.1 mg, 69%).

$^1$H-NMR (D2O, 200 MHz): δ 7.48-7.66 (m, 2H, H-4', H-6'), 7.40 (s, 1H, H-8), 7.31-7.35 (m, 1H, H-5), 7.11-7.19 (m, 2H, H-3', H-5'), 7.03 (s, 1H, H-3), 5.92 (s, 2H, OCH$_2$O).

Example 2

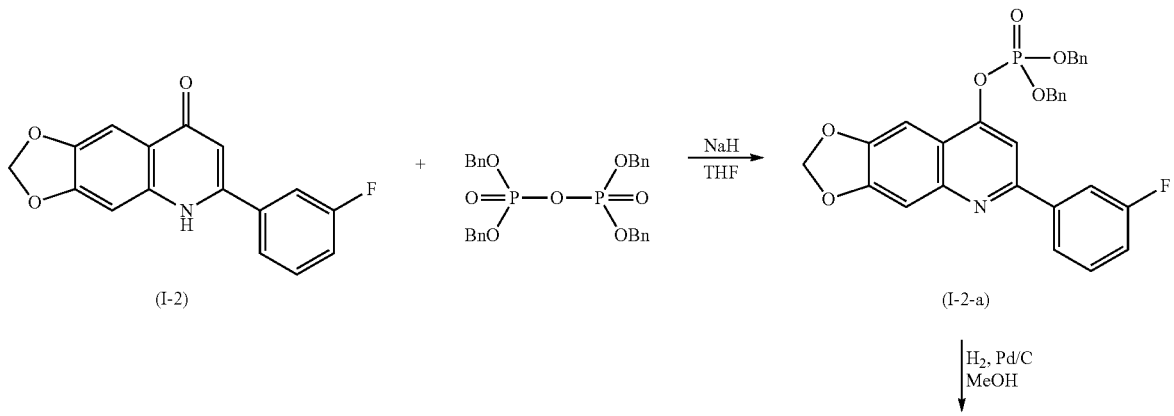

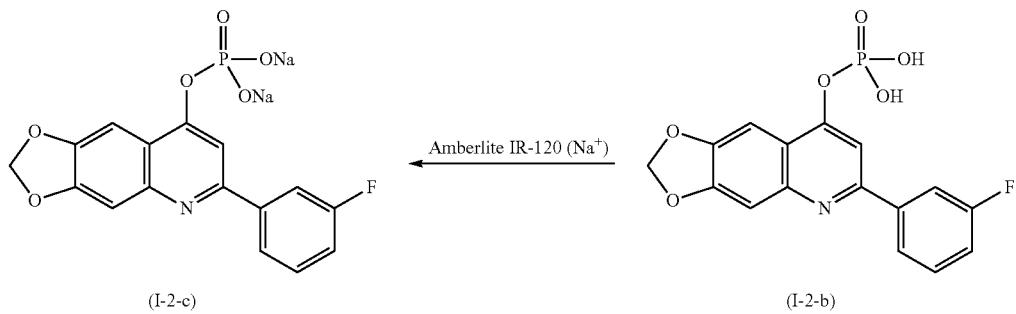

Dibenzyl 2-(3′-fluorophenyl)-6,7-methylenedioxyquinolin-4-yl-phosphate (I-2-a)

Sodium hydride (13.7 mg, 0.57 mmol) was added at 0° C. to a stirred solution of compound I-2 (64.5 mg, 0.23 mmol) in dry tetrahydrofuran (10 ml). After 1 h, tetrabenzyl pyrophosphate (100 mg, 0.19 mmol) was added and the stirring was continued for 20 min.

The mixture was filtered, and the filtrate was concentrated under vacuum at a temperature below 35° C. The residue was dissolved in dichloromethane, washed with an aqueous solution of sodium hydrogen carbonate, dried over $MgSO_4$ and concentrated under vacuum to give compound I-2-a (85.6 mg, 83%).

MP 94-96° C.

$^1$H-NMR (DMSO-d6, 200 MHz): δ 7.61-7.78 (m, 2H, H-2′, H-4′), 7.48-7.56 (m, 1H, H-5′), 7.24-7.45 (m, 13H, H-5, H-8, H-6′, Ph), 7.10 (s, 1H, H-3), 6.21 (s, 2H, $OCH_2O$), 5.29 (s, 2H, —$CH_2$-Ph), 5.24 (s, 2H, —$CH_2$-Ph)

MS (m/z) 544 (ES+)

Anal. calcd for $C_{30}H_{25}FNO_6P$: C, 66.30; H, 4.27; N, 2.58. Found: C, 66.25; H, 4.34; N, 2.55.

2-(3′-Fluorophenyl)-6,7-methylenedioxyquinolin-4-yl-phosphate (I-2-b)

A suspension of compound I-2-a (97.7 mg, 0.18 mmol) in anhydrous MeOH (10 ml) was submitted to hydrogenation in the presence of 10% Pd/C (50 mg) at room temperature for 10 min. The catalyst and precipitates was collected and dissolved in 10% $NaHCO_3$ solution then filtered. The filtrate was acidified with dil HCl, the solid was then collected by filtration and washed with acetone to give compound I-2-b (60.8 mg, 93.1%).

MP>300° C.

$^1$H-NMR (DMSO-d6, 200 MHz): δ 7.91 (s, 1H, H-2′), 7.87 (s, 1H, H-4′), 7.83 (s, 1H, H-5′), 7.50-7.62 (m, 2H, H-5, H-8), 7.25-7.36 (m, 2H, H-5′, H-6′), 6.24 (s, 2H, $OCH_2O$).

MS (m/z) 362 (ES−)

Anal. calcd for $C_{16}H_{13}FNO_6P$: C, 52.91; H, 3.05; N, 3.86. Found: C, 52.86; H, 3.12; N, 3.79.

Sodium 2-(3′-fluorophenyl)-6,7-methylenedioxyquinoline 4-yl-phosphate (I-2-c)

Compound I-2-b was added to a mixture of 20 ml Amberlite IR-120 ($Na^+$ form) and 20 ml water, and then stirred for 6 h at room temperature. The mixture was then filtered to remove Amberlite, and then lyophilized to give I-2-c (68.2 mg, 71%).

$^1$H-NMR (D2O, 200 MHz): δ 7.26-7.78 (m, 5H, H-5, H-8, H-2′, H-5′, H-6′), 6.90-6.96 (m, 2H, H-3, H-4′), 6.03 (s, 2H, $OCH_2O$).

Example 3

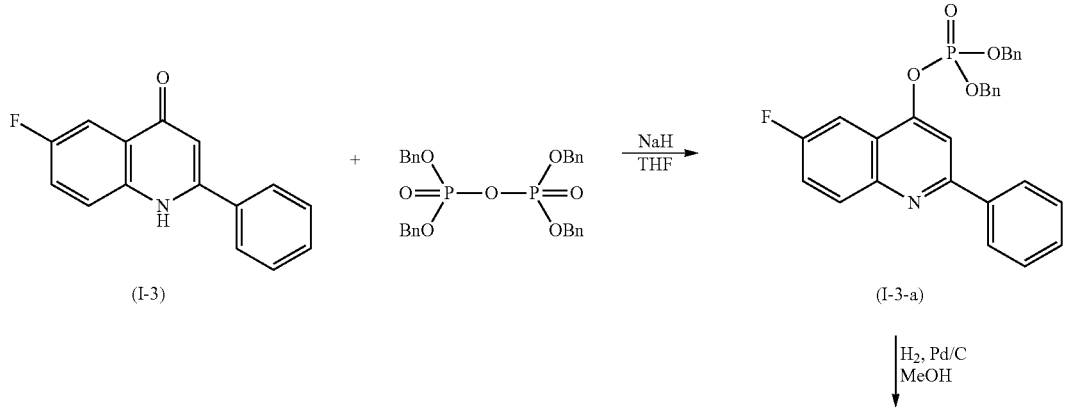

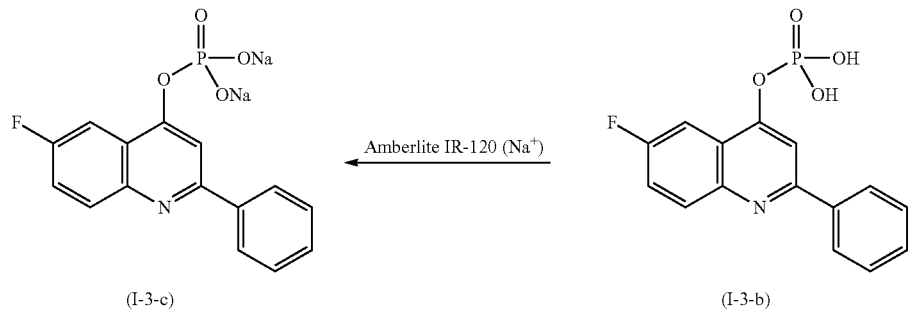

Dibenzyl 6-fluoro-2-phenylquinolin-4-yl-phosphate (I-3-a)

Sodium hydride (13.7 mg, 0.57 mmol) was added at 0° C. to a stirred solution of compound I-3 (55.0 mg, 0.23 mmol) in dry tetrahydrofuran (10 ml). After 1 h, tetrabenzyl pyrophosphate (100 mg, 0.19 mmol) was added and the stirring was continued for 20 min.

The mixture was filtered, and the filtrate was concentrated under vacuum at a temperature below 35° C. The residue was dissolved in dichloromethane, washed with an aqueous solution of sodium hydrogen carbonate, dried over MgSO$_4$ and concentrated under vacuum to give I-3-a as a colorless oil compound (84.4 mg, 89%).

$^1$H-NMR (DMSO-d6, 200 MHz): δ 8.07-8.14 (m, 1H, H-8), 7.92-7.97 (m, 2H, H-2', H-6'), 7.67-7.77 (m, 2H, H-3', H-5'), 7.40-7.50 (m, 10H, Ph), 5.31 (s, 2H, —CH$_2$-Ph), 5.27 (s, 2H, —CH$_2$-Ph)

MS (m/z) 500 (ES+)

Anal. calcd for C$_{29}$H$_{23}$FNO$_6$P: C, 69.74; H, 4.64; N, 2.80. Found: C, 69.75; H, 4.60; N, 2.81.

6-Fluoro-2-phenylquinolin-4-yl-phosphate (I-3-b)

A suspension of compound I-3-a (89.8 mg, 0.18 mmol) in anhydrous MeOH (10 ml) was submitted to hydrogenation in the presence of 10% Pd/C (50 mg) at room temperature for 10 min. The catalyst and precipitates was collected and dissolved in 10% NaHCO$_3$ solution then filtered. The filtrate was acidified with dil HCl, the solid was then collected by filtration and washed with acetone to give compound I-3-b. (50.5 mg, 88%).

MP>300° C.

$^1$H-NMR (DMSO-d6, 200 MHz): δ 8.07-8.14 (m, 3H, H-8, H-2', H-6'), 7.95 (s, 1H, H-5), 7.70-7.74 (m, 2H, H-3', H-5'), 7.50-7.56 (m, 3H, H-3, H-7, H-4')

MS (m/z) 318 (ES−)

Anal. calcd for C$_{15}$H$_{11}$FNO$_4$P: C, 56.44; H, 3.47; N, 4.39. Found: C, 56.42; H, 3.49; N, 4.30.

Sodium 6-Fluoro-2-phenylquinolin-4-yl-phosphate (I-3-c)

Compound I-3-b was added to a mixture of 20 ml Amberlite IR-120 (Na$^+$ form) and 20 ml water, and then stirred for 6 h at room temperature. The mixture was then filtered to remove Amberlite, and then lyophilized to give I-3-c (41.9 mg, 73%).

$^1$H-NMR (D2O, 200 MHz): δ 7.20-7.83 (m, 5H, H-5, H-7, H-8, H-2', H-6'), 7.25-7.31 (m, 4H, H-3, H-3', H-4', H-5').

Example 4

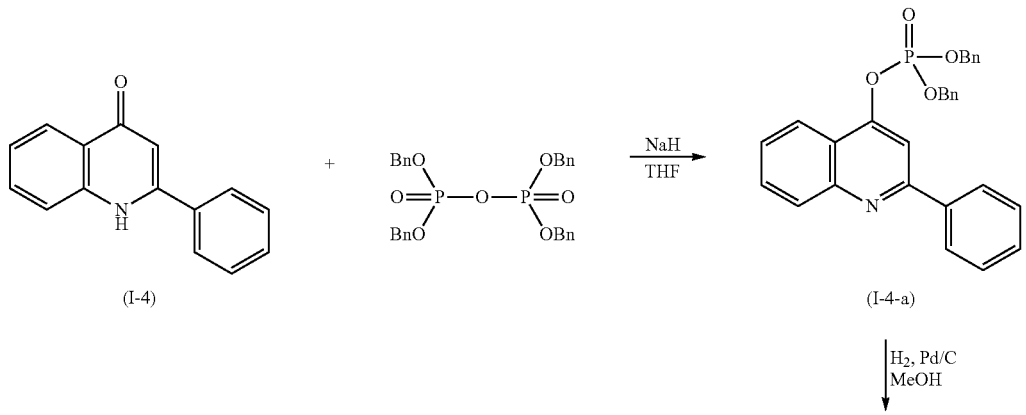

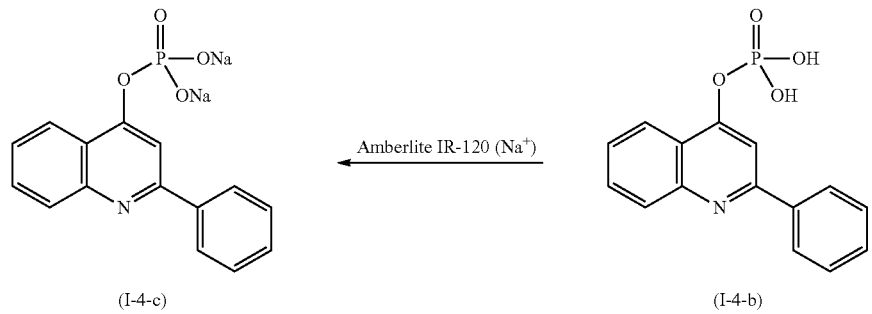

(I-4-c) ← Amberlite IR-120 (Na⁺) ← (I-4-b)

Dibenzyl 2-phenylquinolin-4-yl-phosphate (I-4-a)

Sodium hydride (13.7 mg, 0.57 mmol) was added at 0° C. to a stirred solution of compound I-4 (50.8 mg, 0.23 mmol) in dry tetrahydrofuran (10 ml). After 1 h, tetrabenzyl pyrophosphate (100 mg, 0.19 mmol) was added and the stirring was continued for 20 min.

The mixture was filtered, and the filtrate was concentrated under vacuum at a temperature below 35° C. The residue was dissolved in dichloromethane, washed with an aqueous solution of sodium hydrogen carbonate, dried over $MgSO_4$ and concentrated under vacuum to give I-4-a as a colorless oil compound (71.3 mg, 78%).

$^1$H-NMR (DMSO-d6, 200 MHz): δ 8.05 (d, J=8.2 Hz, 1H, H-5), 7.73-7.98 (m, 5H, H-6, H-7, H-8, H-2', H-6'), 7.58 (d, J=8.0 Hz, 1H, H-4'), 7.48-7.51 (m, 3H, H-3, H-3', H-5'), 7.29-7.40 (m, 10H, Ph), 5.31 (s, 2H, —CH$_2$-Ph), 5.27 (s, 2H, —CH$_2$-Ph)

MS (m/z) 482 (ES+)

Anal. calcd for $C_{29}H_{24}NO_6P$: C, 72.34; H, 5.02; N, 2.90. Found: C, 71.89; H, 5.13; N, 2.88.

2-Phenylquinolin-4-yl-phosphate (I-4-b)

A suspension of compound I-4-a (86.6 mg, 0.18 mmol) in anhydrous MeOH (10 ml) was submitted to hydrogenation in the presence of 10% Pd/C (50 mg) at room temperature for 10 min. The catalyst and precipitates was collected and dissolved in 10% $NaHCO_3$ solution then filtered. The filtrate was acidified with dil HCl, the solid was then collected by filtration and washed with acetone to give compound I-4-b (48.9 mg, 90.3%).

MP>300° C.

$^1$H-NMR (DMSO-d6, 200 MHz): δ 7.80-8.12 (m, 4H, H-5, H-8, H-2', H-6'), 7.49-7.78 (m, 6H, H-3, H-6, H-7, H-3', H-4', H-5'), 7.78 (s, 1H, H-7), 7.66 (t, J=8.0 Hz), 7.42-7.50 (m, 4H, H-3, H-3', H-4', H-5')

MS (m/z) 300 (ES−)

Anal. calcd for $C_{15}H_{12}NO_6P$: C, 59.81; H, 4.02; N, 4.65. Found: C, 59.52; H, 4.13; N, 4.72.

Sodium 6-fluoro-2-phenylquinolin-4-yl-phosphate (I-4-c)

Compound I-4-b was added to a mixture of 20 ml Amberlite

IR-120 (Na⁺ form) and 20 ml water, and then stirred for 6 h at room temperature. The mixture was then filtered to remove Amberlite, and then lyophilized to give I-4-c (41.2 mg, 74%).

$^1$H-NMR (D2O, 200 MHz): δ 8.21 (d, J=8.2 Hz, 1H, H-5), 7.80-7.89 (m, 3H, H-8, H-2', H-6'), 7.78 (s, 1H, H-7), 7.66 (t, J=8.0 Hz), 7.42-7.50 (m, 4H, H-3, H-3', H-4', H-5')

Example 5

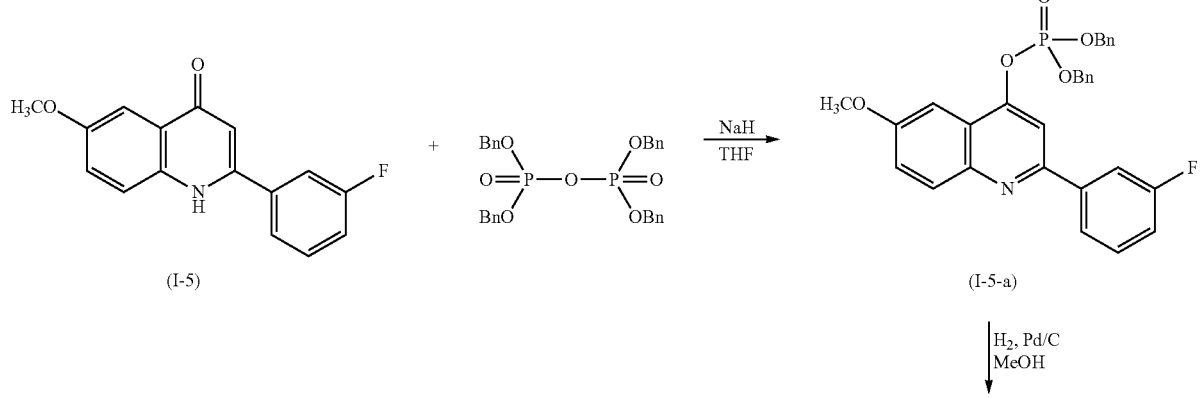

(I-5) + (BnO)$_2$P(O)—O—P(O)(OBn)$_2$ →(NaH/THF)→ (I-5-a) →(H$_2$, Pd/C, MeOH)→

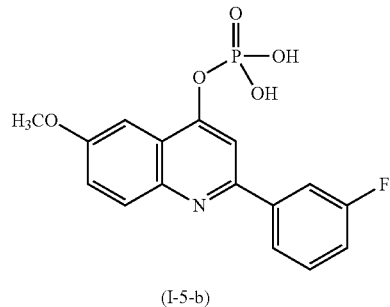

(I-5-b)

15

Dibenzyl 6-methoxy-2(3-'fluorophenyl)-quinolin-4-yl-phosphate (I-5-a)

Sodium hydride (13.7 mg, 0.57 mmol) was added at 0° C. to a stirred solution of compound I-5 (61.9 mg, 0.23 mmol) in dry tetrahydrofuran (10 ml). After 1 h, tetrabenzyl pyrophosphate (100 mg, 0.19 mmol) was added and the stirring was continued for 20 min.

The mixture was filtered, and the filtrate was concentrated under vacuum at a temperature below 35° C. The residue was dissolved in dichloromethane, washed with an aqueous solution of sodium hydrogen carbonate, dried over MgSO$_4$ and concentrated under vacuum to give I-5-a as a colorless oil compound (85.4 mg, 85%)

$^1$H-NMR (DMSO-d6, 200 MHz): δ 7.98 (d, J=9.4 Hz, 1H, H-8), 7.74-7.83 (m, 3H, H-5, H-7, H-5'), 7.43-7.54 (m, 1H, H-6'), 7.41-7.48 (m, 1H, H-2'), 7.20-7.22 (m, H-3), 5.31 (s, 2H, —CH$_2$-Ph), 5.27 (s, 2H, —CH$_2$-Ph), 3.78 (s, 3H, OCH$_3$).

MS (m/z) 530 (ES+)

Anal. calcd for C$_{30}$H$_{25}$FNO$_5$P: C, 68.05; H, 4.76; N, 2.65. Found: C, 67.32; H, 4.33; N, 2.78.

6-Methoxy-2(3-'fluorophenyl)-quinolin-4-yl-phosphate (I-5-b)

A suspension of compound I-5-a (95.2 mg, 0.18 mmol) in anhydrous MeOH (10 ml) was submitted to hydrogenation in the presence of 10% Pd/C (50 mg) at room temperature for 10 min. The catalyst and precipitates was collected and dissolved in 10% NaHCO$_3$ solution then filtered. The filtrate was acidified with dil HCl, the solid was then collected by filtration and washed with acetone to give compound I-5-b (56.5 mg, 89.9%).

MP>300° C.

$^1$H-NMR (DMSO-d6, 200 MHz): δ 7.93-7.89 (m, 4H, H-5, H-7, H-8, H-5'), 7.45-7.58 (m, 1H, H-6'), 7.35-7.41 (m, 2H, H-2', H-4'), 7.20-7.32 (m, 1H, H-3), 3.81 (s, 3H, OCH$_3$)

MS (m/z) 348 (ES−)

Anal. calcd for C$_{16}$H$_{13}$FNO$_5$P: C, 55.02; H, 3.75; N, 4.01. Found: C, 54.90; H, 3.89; N, 4.35.

Example 6

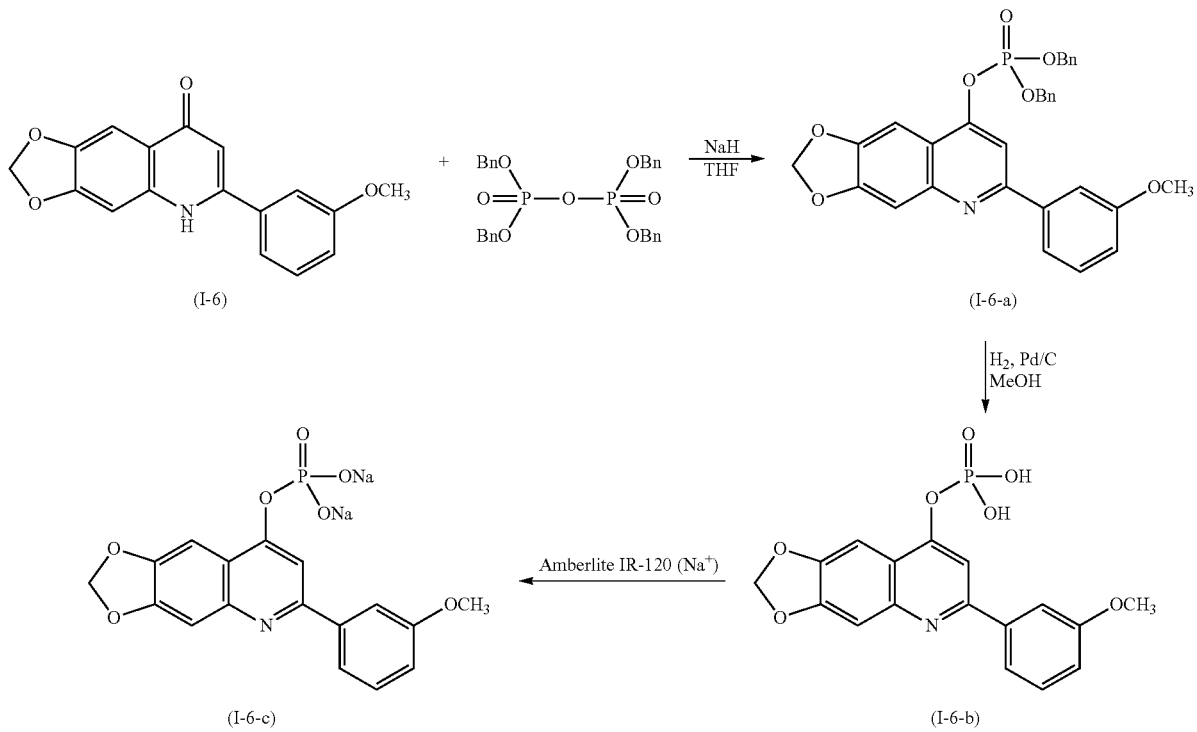

Dibenzyl 2-(3'-methoxyphenyl)-6,7-methylenedioxyquinolin-4-yl-phosphate (I-6-a)

Sodium hydride (13.7 mg, 0.57 mmol) was added at 0° C. to a stirred solution of compound I-6 (67.9 mg, 0.23 mmol) in dry tetrahydrofuran (10 ml). After 1 h, tetrabenzyl pyrophosphate (100 mg, 0.19 mmol) was added and the stirring was continued for 20 min.

The mixture was filtered, and the filtrate was concentrated under vacuum at a temperature below 35° C. The residue was dissolved in dichloromethane, washed with an aqueous solution of sodium hydrogen carbonate, dried over $MgSO_4$ and concentrated under vacuum to give to give I-6-a as a colorless oil compound (88.6 mg, 84%)

$^1$H-NMR (DMSO-d6, 200 MHz): δ 7.60 (s, 1H, H-6'), 7.55 (s, 1H, H-2'), 7.25-7.40 (m, 14H, H-5, H-8, H-4', H-5', Ph), 6.21 (s, 2H, $OCH_2O$), 5.28 (s, 2H, —$CH_2$-Ph), 5.24 (s, 2H, —$CH_2$-Ph), 3.80 (s, 3H, $OCH_3$)

MS (m/z) 556 (ES+)

Anal. calcd for $C_{31}H_{26}NO_7P$: C, 67.02; H, 4.72; N, 2.52. Found: C, 68.15; H, 4.68; N, 2.61.

2-(3'-Methoxyphenyl)-6,7-methylenedioxyquinolin-4-yl-phosphate (I-6-b)

A suspension of compound I-6-a (97.74 mg, 0.18 mmol) in anhydrous MeOH (10 ml) was submitted to hydrogenation in the presence of 10% Pd/C (50 mg) at room temperature for 10 min. The catalyst and precipitates was collected and dissolved in 10% $NaHCO_3$ solution then filtered. The filtrate was acidified with dil HCl, the solid was then collected by filtration and washed with acetone to give compound I-6-b (63.5 mg, 94%).

MP>300° C.

MS (m/z) 374 (ES−)

Anal. calcd for $C_{17}H_{14}NO_7P$: C, 54.41; H, 3.76; N, 3.73. Found: C, 53.86; H, 3.66; N, 3.81.

Sodium 2-(3'-methoxyphenyl)-6,7-methylenedioxyquinolin-4-yl-phosphate (I-6-c)

Compound I-6-b was added to a mixture of 20 ml Amberlite IR-120 ($Na^+$ form) and 20 ml water, and then stirred for 6 h at room temperature. The mixture was then filtered to remove Amberlite, and then lyophilized to give I-6-c (53.9 mg, 76%).

$^1$H-NMR (D2O, 200 MHz): δ 7.56 (s, 1H, H-6'), 7.25-7.42 (m, 4H, H-5, H-8, H-2', H-5'), 7.16 (s, 1H, H-4'), 6.95 (s, 1H, H-3), 6.00 (s, 2H, $OCH_2O$), 3.62 (s, 3H, $OCH_3$)

In the following Example 7, a novel intermediate, 2-selenophene 4-quinolone (I-7-d), was synthesized. 2-selenophene-4-quinolone (I-7-d) was reacted with tetrabenzyl pyrophosphate in the presence of alkali, the corresponding phosphoric acid dibenzyl ester (I-7-e) was obtained.

Example 7

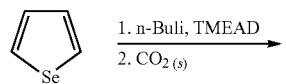

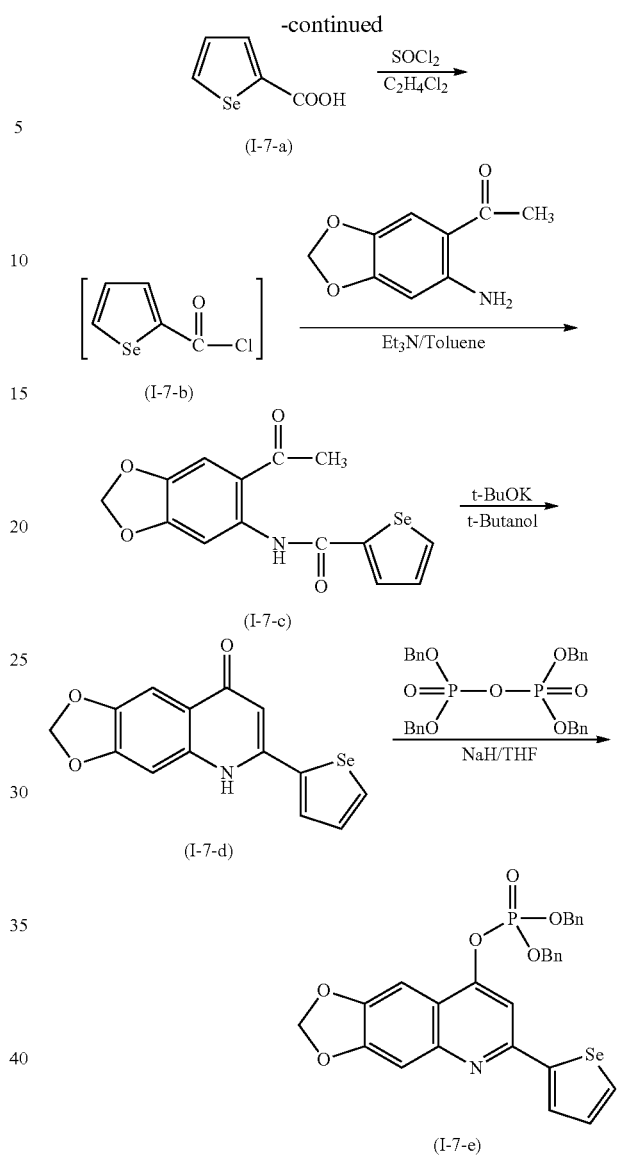

Selenophene-2-carboxylic acid (I-7-a)

To a solution of selenophene (20 g, 152.7 mmol) in $(Et)_2O$ (150 ml) was added TMEDA (25.5 ml, 170.0 mmol) and n-butyllithium (66.1 ml of a 2.5 M solution in hexane, 152.8 mmol). The resulting solution was heated at reflux for 1.5 h, and then cooled in an acetone/$CO_2$ bath, after which crushed solid carbon dioxide (40 g, 909.1 mmol) was added. The reaction mixture was allowed to return to room temperature, and quenched by addition of 10% KOH solution. The aqueous layer was acidified to pH 3 with 8 M HCl, extracted with $(Et)_2O$, washed with brine, dried over $MgSO_4$ filtered and concentrated under vacuum to give compound I-7-a (24.6 g, 92.1%).

MP 122-124° C.

$^1$H-NMR ($CDCl_3$-$d_1$, 200 MHz): δ 8.92 (s, 1H, —COO$\underline{H}$), 8.37 (dd, J=1.0 Hz, 5.6 Hz, 1H, H-3), 8.13 (dd, J=0.8 Hz, 3.8 Hz, 1H, H-5), 7.37 (dd, J=3.8 Hz, 5.6 Hz, 1H, H-4).

MS (m/z) 175.0 (EI+)

Anal. calcd for $C_5H_4O_2Se$: C, 34.31; H, 2.30. Found: C, 34.33; H, 2.28.

N-(5-acetylbenzo[d][1,3]dioxol-6-yl)selenophene-2-carboxamide (I-7-c)

I-7-a (2 g, 11.40 mmol) was taken for subsequent chlorination by refluxing with thionyl chloride (4.1 ml, 56.18 mmol) for 20 h to afford I-7-b, which, without further purification, was treated with 2-amino-(4,5-methylenedioxy)-acetophenone (1.63 g, 9.12 mmol) and triethylamine (2 ml, 14.80 mmol) in 100 ml toluene, and refluxed for 3 h. The reaction mixture was concentrated under vacuum, and the solid material is consecutively washed with ethanol and dried at 80° C. for 2 h to give crude compound I-7-c (2.7 g, 74%).

MP 198.5-198.8° C.

$^1$H-NMR (DMSO-d6, 200 MHz): δ 12.85 (s, 1H, NHCO), 8.52 (d, J=5.1 Hz, 1H, H-3'), 8.16 (s, 1H, H-4), 7.93 (d, J=3.8 Hz, 1H, H-5'), 7.61 (s, 1H, H-7), 7.49-7.46 (m, 1H, H-4'), 6.13 (s, 2H, OCH$_2$O), 2.58 (s, 3H, CH$_3$).

MS (m/z) 336.2 (EI+)

Anal. calcd for C14H11NO4Se: C, 50.01; H, 3.30; N, 4.17. Found: C, 50.11; H, 3.32; N, 4.15.

2-(2'-Selenophenyl)-6,7-(methylenedioxy)-4-quinolone (I-7-d)

I-7-c (2.7 g, 8.0 mmol) was suspended in 100 ml t-BuOH. Potassium tert-butoxide (4.49 g, 40 mmol) was added, and the mixture was heated at reflux for 24 h. The mixture was cooled to room temperature, and poured onto 100 ml of aqueous NH$_4$Cl. The yellow-brown solid was collected and washed by distilled water to give compound I-7-d (3.1 g, 85%).

MP>300° C.

$^1$H-NMR (DMSO-d6, 200 MHz): δ 8.27 (s, 1H, H-3'), 7.83 (s, 1H, H-5'), 7.39 (t, J=4.5 Hz, 1H, H-4'), 7.31 (s, 1H, H-5), 7.14 (s, 1H, H-8), 6.11 (s, 3H, H-3, OCH$_2$O).

MS (m/z) 318.2 (EI+)

Anal. calcd for C14H9NO3Se: C, 52.85; H, 2.85; N, 4.40. Found: C, 52.87; H, 2.82; N, 4.45.

Dibenzyl 2-(2'-selenophenyl)-6,7-methylenedioxyquinolin-4-yl-phosphate (I-7-e)

Sodium hydride (30 mg, 1.25 mmol) was added at 0° C. to a stirred solution of compound I-7-d (100.0 mg, 0.32 mmol) in dry tetrahydrofuran (10 ml). After 1 h, tetrabenzyl pyrophosphate (204.6 mg, 0.38 mmol) was added and the stirring was continued for 20 min.

The mixture was filtered, and the filtrate was concentrated under vacuum at a temperature below 35° C. The residue was dissolved in dichloromethane, washed with an aqueous solution of sodium hydrogen carbonate, dried over MgSO$_4$ and concentrated under vacuum to give the solid which was subjected to silica gel column chromatography. Elution with CH$_2$Cl$_2$ gave yellowish compound I-7-e (151.8 mg, 82%).

MP 110.5-110.8° C.

$^1$H-NMR (DMSO-d6, 200 MHz): δ 8.24 (d, J=5.6 Hz, 1H, H-3'), 7.65 (d, J=3.8 Hz, 1H, H-5'), 7.57 (s, 1H, H-5), 7.05 (s, 1H, H-8), 7.39-7.26 (m, 11H, H-4', Ph), 6.19 (s, 2H, OCH$_2$O), 5.28 (s, 2H, —CH$_2$-Ph), 5.24 (s, 2H, —CH$_2$-Ph).

MS (m/z) 580 (ES+)

Anal. calcd for 28$_0$H$_{22}$NO$_6$PSe: C, 58.14; H, 3.83; N, 2.42. Found: C, 57.28; H, 3.56; N, 2.59.

Example 8

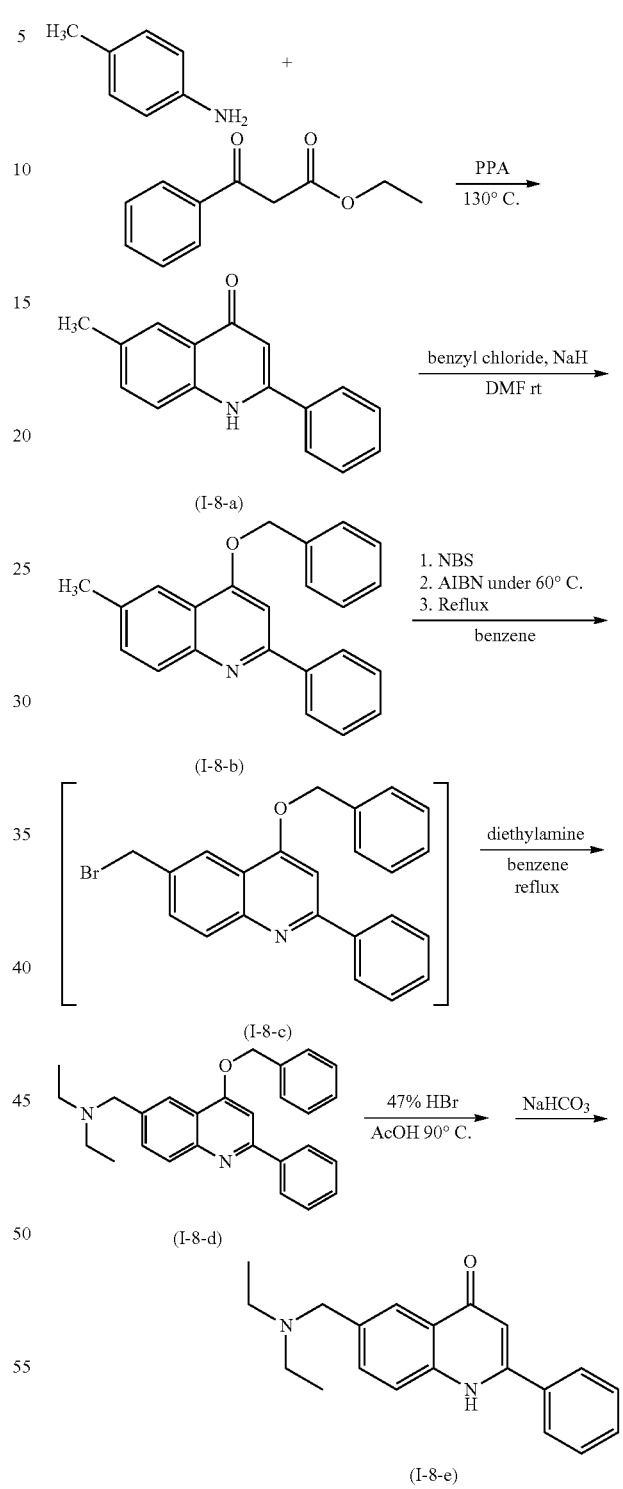

6-Methyl-2-phenylquinolin-4(1H)-one (I-8-a)

A mixture of p-toluidine (2.14 g, 0.02 mole), ethyl benzoylacetate (4.9 g, 0.025 mole), and polyphosphoric acid (PPA) was heated at 130° C. with stirring. After the reaction was complete, the mixture was cooled to room temperature and neutralized with 4 M NaOH. The yellow solid was filtered, washed with water, dried and recrystallized from ethanol to give compound I-8-a as white solid (2.9 g, 48.9%).

MP 290.2-291.5° C.

$^1$H-NMR (DMSO-d6, 200 MHz): δ 11.55 (1H, s, H-1), 7.88 (1H, s, H-5), 7.79-7.82 (2H, m, H-2', H-3'), 7.66 (1H, d, J=8.5 Hz, H-8), 7.54-7.57 (3H, m, H-3', H-4', H-5'), 7.48 (1H, d, J=8.5 Hz, H-7), 6.31 (1H, s, H-3), 2.40 (3H, s, CH$_3$)

MS (m/z) 235 (EI+)

Anal. calcd for C16H13NO: C, 81.68; H, 5.57; N, 5.95. Found: C, 81.60; H, 5.63; N, 5.88.

4-(Benzyloxy)-6-methyl-2-phenylquinoline (I-8-b)

I-8-a (700 mg, 3 mmole) was dissolved in dry DMF (30 ml), and NaH (360 mg, 15 mmole) was added protionwise with stirring for 30 min at room temperature. Benzyl chloride (750 mg, 6 mmole) was then added dropwise, and stirred at room temperature overnight. The reaction mixture was poured into ice-water and extracted with CH$_2$Cl$_2$. The organic layer was washed with water, dried over MgSO$_4$, and evaporated. The residue was further chromatographed over silica gel by elution with n-hexane-EtOAc (3:1), and recrystallized from n-hexane-CH$_2$Cl$_2$ to afford I-8-b as white crystal (536 mg, 54.9%).

MP 138.6-139.3° C.

$^1$H-NMR (DMSO-d6, 200 MHz): δ 8.23-8.26 (2H, m, H-2', H-6'), 7.88-7.91 (2H, m, H-5, H-8), 7.37-7.62 (9H, m, H-7, H-3', H-4', H-5', Ph), 5.51 (2H, s, OCH$_2$Ph), 2.48 (3H, s, CH$_3$)

Anal. calcd for C23H19NO: C, 84.89; H, 5.89; N, 4.30. Found: C, 84.93; H, 5.85; N, 4.33.

N-{[4-(Benzyloxy)-2-phenylquinolin-6-yl]methyl}-N-ethyl ethanamine (I-8-d)

I-8-b (650 mg, 2 mmol), N-bromo-succinimide (NBS, 360 mg, 2 mmol), and 2,2'-azobis(isobutyronitrile) (AIBN, 30 mg, 0.19 mmol) were added to a dry round bottom flask, which was purged with argon. 50 ml of dry benzene was added to the reaction mixture in an argon atmosphere with stirring at room temperature for 30 min, and then refluxed at 80° C. for 1 h and then cooled to room temperature to give I-7-c, which, without further purification, was treated with diethylamine (3.0 ml, 29.0 mmole), and then refluxed for 1 h. After removing the solvent by evaporation, the mixture was partitioned with EtOAc and 50 ml 10% HCl., and then the acid layer was neutralized to PH 7-8 by 10% NaHCO$_3$, extracted with EtOAc (100 ml×5). The organic layer was dried over MgSO$_4$, and evaporated. The residue was further chromatographed over silica gel by elution with CH$_2$Cl$_2$-methanol (3:1), and recrystallized from n-hexane-EtOAc to afford I-8-d as light-yellow solid (120 mg, 15.1%).

MP 107.7-108.6° C.

$^1$H-NMR (DMSO-d6, 200 MHz): δ 8.22 (2H, m, H-2', H-6'), 8.01 (1H, s, H-5), 7.91 (1H, d, H-8), 7.33-7.69 (9H, m, H-7, H-3', H-4', H-5', Ph), 5.49 (2H, s, OCH$_2$Ph), 3.65 (2H, s, CH$_2$N(CH$_2$CH$_3$)$_2$), 2.43 (4H, q, J=7 Hz, CH$_2$N(CH$_2$CH$_3$)$_2$), 0.93 (6H, t, J=7 Hz, CH$_2$N(CH$_2$CH$_3$)$_2$)

MS (m/z) 396 (EI+)

Anal. calcd for C27H28N2O: C, 81.78; H, 7.12; N, 7.06. Found: C, 81.68; H, 7.03; N, 7.15.

6-[(Diethylamino)methyl]-2-phenylquinolin-4(1H)-one (I-8-e)

I-8-d (120 mg, 0.3 mmol) was dissolved in glacial acetic acid (5 ml). HBr (3 ml) was added while the solution was heated to 60° C., and the mixture was heated to 90° C. for 3 h. After the reaction was complete, the reaction mixture was poured into water, and extracted with EtOAc. The acid layer was neutralized to pH 7-8 by adding 10% NaHCO$_3$, and extracted with EtOAc (100 ml×5). The organic layer was dried over MgSO$_4$, and evaporated. The residue was recrystallized from n-hexane-EtOAc to afford I-8-d as gray solid (55 mg, 59.9%).

MP 227.9-229.7° C.

$^1$H-NMR (DMSO-d6, 200 MHz): δ 7.96 (1H, s, H-5), 7.78 (2H, in, H-2', H-6'), 7.69 (1H, d, H-8), 7.50-7.58 (4H, m, H-7, H-3', H-4', H-5'), 6.31 (1H, s, H-3), 3.55 (2H, s, CH$_2$N(CH$_2$CH$_3$)$_2$), 2.41 (4H, q, J=7 Hz, CH$_2$N(CH$_2$CH$_3$)$_2$), 0.92 (6H, t, J=7 Hz, CH$_2$N(CH$_2$CH$_3$)$_2$)

MS (m/z) 306 (EI+)

Anal. calcd for C20H22N2O: C, 78.40; H, 7.24; N, 9.14. Found: C, 78.43; H, 7.35; N, 9.08.

Example 9

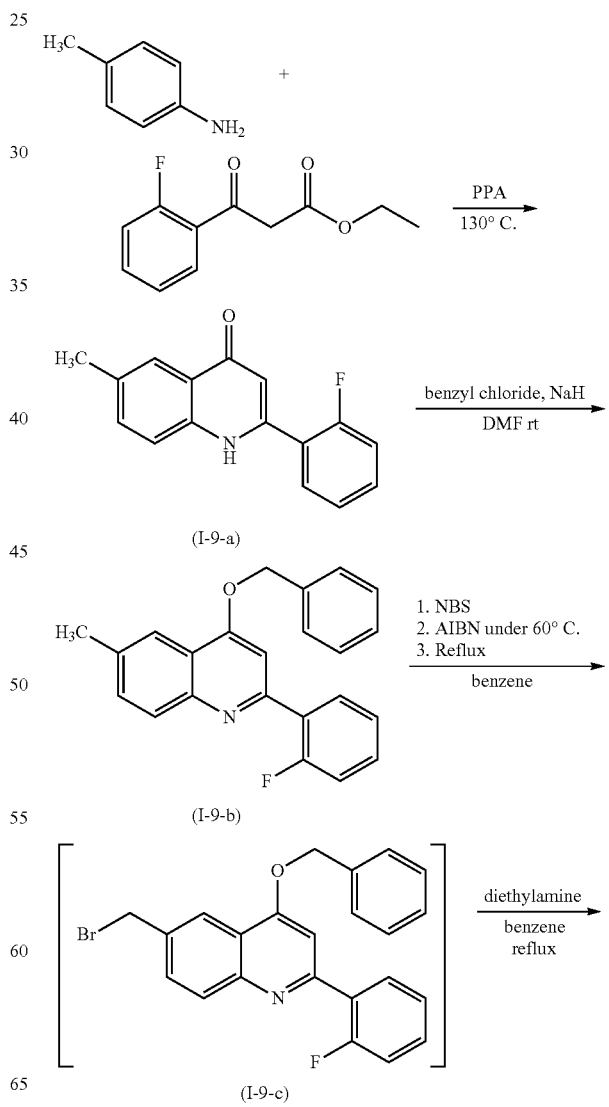

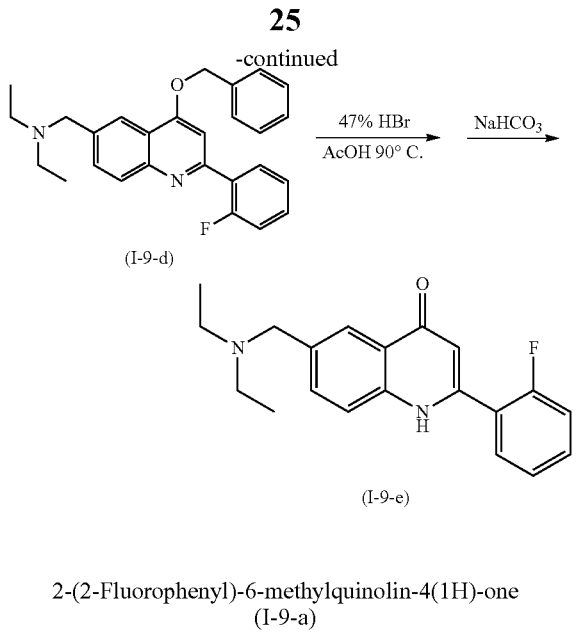

2-(2-Fluorophenyl)-6-methylquinolin-4(1H)-one (I-9-a)

A mixture of p-toluidine (2.14 g, 0.02 mole), 2-fluoro-ethyl benzoylacetate (5.25 g, 0.025 mole), and polyphosphoric acid (PPA) was heated at 130° C. with stirring. After the reaction was complete, the mixture was cooled to room temperature and neutralized with 4 M NaOH. The yellow solid was filtered, washed with water, dried and recrystallized from ethanol to give compound I-9-a as white solid (2.6 g, 51.3%).

MP 259.1-259.9° C.

$^1$H-NMR (DMSO-d6, 200 MHz): δ7.86 (1H, s, H-5), 7.64 (1H, td, J=7.58, H-4'), 7.47-7.57 (3H, m, H-7, H-8, H-6'), 7.30-7.43 (2H, d, J=7.02, dd, J=7.36, H-3', 5'), 6.12 (1H, s, H-3), 2.36 (3H, s, CH$_3$)

MS (m/z) 253 (EI+)

Anal. calcd for C16H22FNO: C, 75.88; H, 4.78; N, 5.53. Found: C, 75.94; H, 4.70; N, 5.46.

4-(Benzyloxy)-2-(2-fluorophenyl)-6-methylquinoline (I-9-b)

I-9-a (750 mg, 3 mmole) was dissolved in dry DMF (30 ml), and NaH (360 mg, 15 mmole) was added portionwise with stirring for 30 min at room temperature. Benzyl chloride (750 mg, 6 mmole) was then added dropwise, and stirred at room temperature overnight. The reaction mixture was poured into ice-water and extracted with CH$_2$Cl$_2$. The organic layer was washed with water, dried over MgSO$_4$, and evaporated. The residue was further chromatographed over silica gel by elution with n-hexane-EtOAc (3:1), and recrystallized from n-hexane-CH$_2$Cl$_2$ to afford I-9-b as white crystal (515 mg, 50.0%).

MP 91.5-92.8° C.

$^1$H-NMR (DMSO-d6, 200 MHz): δ 7.84-7.97 (3H, m, H-5, H-8, H-4'), 7.26-7.58 (10H, m, H-3, H-7, H-3', H-5', H-6', Ph), 5.38 (2H, s, OCH$_2$Ph), 2.45 (3H, s, CH$_3$)

MS (m/z) 343 (EI+)

Anal. calcd for C23H18FNO: C, 80.45; H, 5.28; N, 4.08. Found: C, 80.51; H, 5.29; N, 4.17.

N-{[4-(Benzyloxy)-2-(2-fluorophenyl)quinolin-6-yl]methyl}-N-ethylethanamine (I-9-d)

I-9-b (680 mg, 2 mmol), N-bromo-succinimide (NBS, 360 mg, 2 mmol), and 2,2'-azobis(isobutyronitrile) (AIBN, 30 mg, 0.19 mmol) were added to a dry round bottom flask, which was purged with argon. 50 ml of dry benzene was added to the reaction mixture in an argon atmosphere with stirring at room temperature for 30 min, and then refluxed at 80° C. for 1 h and then cooled to room temperature to give I-9-c, which, without further purification, was treated with diethylamine (3.0 ml, 29.0 mmole), and then refluxed for 1 h. After removing the solvent by evaporation, the mixture was partitioned with EtOAc and 50 ml 10% HCl., and then the acid layer was neutralized to PH 7-8 by 10% NaHCO$_3$, extracted with EtOAc (100 ml×5). The organic layer was dried over MgSO$_4$, and evaporated. The residue was further chromatographed over silica gel by elution with CH$_2$Cl$_2$-methanol (3:1), and recrystallized from n-hexane-EtOAc to afford I-9-d as yellow solid (120 mg, 15.1%).

MP 51.2-51.5° C.

$^1$H-NMR (DMSO-d6, 200 MHz): δ 8.04 (1H, s, H-5), 7.84-7.96 (2H, m, H-8, H-5'), 7.69 (1H, dd, H-4'), 7.28-7.54 (9H, m, H-3, H-7, H-3', H-6', Ph), 5.41 (2H, s, OCH$_2$Ph), 3.68 (2H, s, CH$_2$N(CH$_2$CH$_3$)$_2$), 2.46 (4H, q, J=7, CH$_2$N(CH$_2$CH$_3$)$_2$), 0.94 (6H, t, J=7, CH$_2$N(CH$_2$CH$_3$)$_2$)

MS (m/z) 414 (EI+)

Anal. calcd for C27H27FN2O: C, 78.23; H, 6.57; N, 6.76. Found: C, 78.25; H, 6.67; N, 6.74.

6-[(Diethylamino)methyl]-2-(2-fluorophenyl)quinolin-4(1H)-one (I-9-e)

I-9-d (120 mg, 0.3 mmol) was dissolved in glacial acetic acid (5 ml). HBr (3 ml) was added while the solution was heated to 60° C., and the mixture was heated to 90° C. for 3 h. After the reaction was complete, the reaction mixture was poured into water, and extracted with EtOAc. The acid layer was neutralized to pH 7-8 by adding 10% NaHCO$_3$, and extracted with EtOAc (100 ml×5). The organic layer was dried over MgSO$_4$, and evaporated. The residue was recrystallized from n-hexane-EtOAc to afford I-8-e as gray solid (58 mg, 59.6%). MP 184.2-184.7° C.

$^1$H-NMR (DMSO-d6, 200 MHz): δ 11.9 (1H, s, H-1), 7.97 (1H, s, H-5), 7.52-7.69 (4I-1, m, H-7, H-8, H-4', H-6'), 7.31-7.43 (2H, m, H-3', H-5'), 6.12 (1H, s, H-3), 3.57 (2H, s, CH$_2$N(CH$_2$CH$_3$)$_2$), 2.40 (4H, q, J=7 Hz, CH$_2$N(CH$_2$CH$_3$)$_2$), 0.92 (6H, t, J=7 Hz, CH$_2$N(CH$_2$CH$_3$)$_2$)

MS (m/z) 324 (EI+)

Anal. calcd for C20H21FN2O: C, 74.05; H, 6.53; N, 8.64. Found: C, 73.94; H, 6.62; N, 8.67.

Example 10

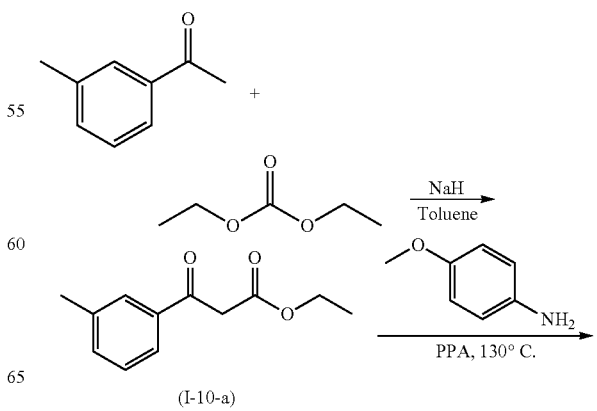

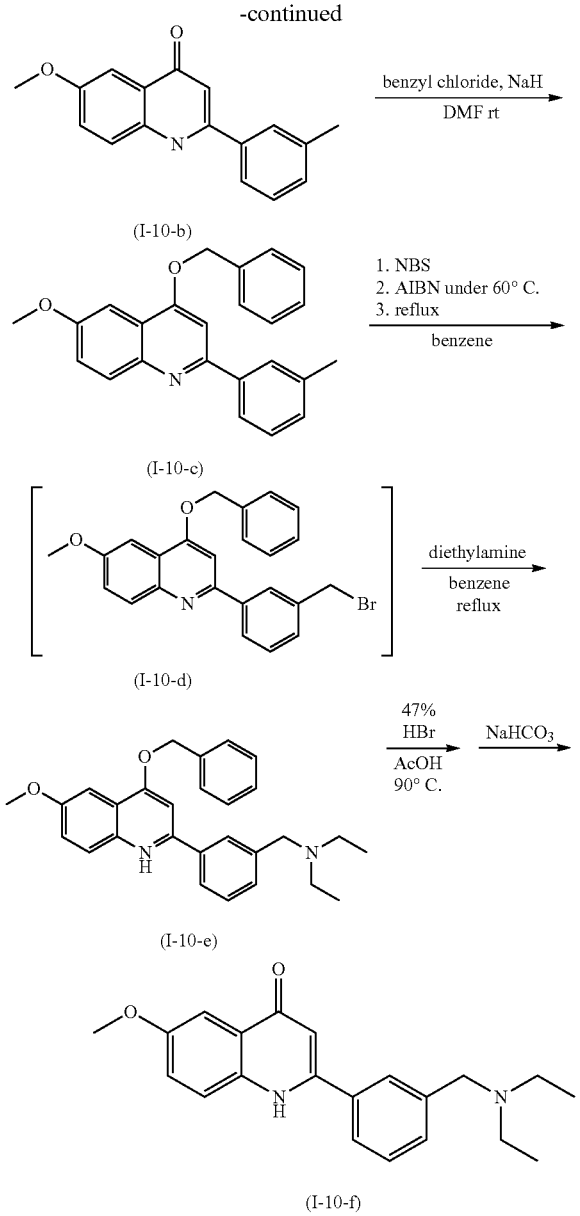

MS (m/z) 206 (EI+)
Anal. calcd for C12H14O3: C, 69.88; H, 6.84. Found: C, 69.72; H, 6.95.

6-Methoxy-2-m-tolylquinolin-4(1H)-one (I-10-b)

A mixture of p-anisidine (2.14 g, 0.02 mole), I-10-a (5.1 g, 0.025 mole), and polyphosphoric acid (PPA) was heated at 130° C. with stirring. After the reaction was complete, the mixture was cooled to room temperature and neutralized with 4 M NaOH. The yellow solid was filtered, washed with water, dried and recrystallized from ethanol to give compound I-9-a as light-purple solid (2.6 g, 25.8%).
MP 262.2-264.1° C.
$^1$H-NMR (DMSO-d6, 200 MHz): δ 7.70 (1H, d, H-8), 7.55-7.60 (2H, m, H-5, 7), 7.25-7.47 (4H, m, H-2', H-4', H-5', H-6'), 6.33 (1H, s, H-3), 3.80 (3H, s, OCH$_3$), 2.37 (3H, s, CH$_3$)
MS (m/z) 265 (EI+)
Anal. calcd for C17H15NO: C, 76.79; H, 5.70; N, 5.28. Found: C, 76.81; 5.62; N, 5.34.

4-(Benzyloxy)-6-methoxy-2-m-tolylquinoline (I-10-c)

I-10-b (795 mg, 3 mmole) was dissolved in dry DMF (30 ml), and NaH (360 mg, 15 mmole) was added portionwise with stirring for 30 min at room temperature. Benzyl chloride (750 mg, 6 mmole) was then added dropwise, and stirred at room temperature overnight. The reaction mixture was poured into ice-water and extracted with CH$_2$Cl$_2$. The organic layer was washed with water, dried over MgSO$_4$, and evaporated. The residue was further chromatographed over silica gel by elution with n-hexane-EtOAc (3:1), and recrystallized from n-hexane-CH$_2$Cl$_2$ to afford I-10-c as white crystal (530 mg, 49.7%).
MP 133.0-134° C.
$^1$H-NMR (DMSO-d6, 200 MHz): δ 8.00 (1H, s, H-5), 7.96 (1H, d, H-8), 7.89 (1H, d, J=8 Hz, H-7), 7.32-7.58 (6H, m, H-3, H-2', H-5', H-6', Ph), 7.22 (1H, d, J=7 Hz, H-4'), 5.50 (2H, s, OCH$_2$Ph), 3.83 (3H, s, OCH3), δ2.38 (3H, s, CH$_3$)
MS (m/z) 355 (EI+)
Anal. calcd for C24H21NO2: C, 81.10; H, 5.96; N, 3.94. Found: C, 81.9; H, 5.81; N, 3.97.

N-{[3-(4-(Benzyloxy)-6-methoxyquinolin-2-yl)phenyl)methyl}-N-ethylethanamine (I-10-e)

I-10-c (530 mg, 2 mmol), N-bromo-succinimide (NBS, 360 mg, 2 mmol), and 2,2'-azobis(isobutyronitrile) (AIBN, 30 mg, 0.19 mmol) were added to a dry round bottom flask, which was purged with argon. 50 ml of dry benzene was added to the reaction mixture in an argon atmosphere with stirring at room temperature for 30 min, and then refluxed at 80° C. for 1 h and then cooled to room temperature to give I-10-d, which, without further purification, was treated with diethylamine (3.0 ml, 29.0 mmole), and then refluxed for 1 h. After removing the solvent by evaporation, the mixture was partitioned with EtOAc and 50 ml 10% HCl., and then the acid layer was neutralized to PH 7-8 by 10% NaHCO$_3$, extracted with EtOAc (100 ml×5). The organic layer was dried over MgSO$_4$, and evaporated. The residue was further chromatographed over silica gel by elution with CH$_2$Cl$_2$-methanol (3:1), and recrystallized from n-hexane-EtOAc to afford I-10-e as yellow solid (25 mg, 2.9%).
MP 89.2-89.5° C.

Ethyl 3-methyl-benzoyl-acetate (I-10-a)

To a vigorously stirred suspension of NaH (564 mg, 48.5 mmol) and CO(OEt)$_2$ (5.73 g, 48.5 mmol) in anhydrous toluene (50 ml) was added dropwise a solution of 3-methylacetophenone (4.33 g, 32.3 mmole) in toluene under reflux. The mixture was allowed to reflux and was stirred for 30 min after the addition was complete. When cooled to room temperature, the mixture was acidified with glacial AcOH. After ice-cold water was added, the mixture was extracted with toluene. The organic layer was dried over MgSO$_4$, and evaporated. The residue was further chromatographed over silica gel by elution with CH$_2$Cl$_2$-n-haxane (3:2) to afford I-10-b as light-yellow liquid (3.13 g, 46.9%)
$^1$H-NMR (DMSO-d6, 200 MHz): δ 7.68-7.72 (2H, m, H-4, H-6), 7.32-7.36 (2H, m, H-2, H-3), 4.16 (2H, q, J=7, CH$_2$CH$_3$), 3.94 (2H, s, H-10), 2.38 (3H, s, CH$_3$), 1.2 (3H, t, J=7, CH$_2$CH$_3$)

$^1$H-NMR (DMSO-d6, 200 MHz): δ 8.13 (1H, s, H-3). 7.87-8.04 (2H, m, H-7, 8), 7.34-7.43 (10H, m, H-3, H-2', H-4', H-5', H-6', Ph), 5.51 (2H, s, OCH$_2$Ph), 3.84 (3H, s, OCH$_3$), 3.69 (2H, s, CH$_2$N(CH$_2$CH$_3$)$_2$), 2.53 (4H, q, J=7 Hz, CH$_2$N (CH$_2$CH$_3$)$_2$), 0.99 (6H, t, J=7 Hz, CH$_2$N(CH$_2$CH$_3$)$_2$)

MS (m/z) 426 (EI+)

Anal. calcd for C28H30N2O2: C, 78.83; H, 7.90; N, 6.57. Found: C, 78.95; H, 7.14; N, 6.48.

2-{3-[(Diethylamino)methyl]phenyl}-6-methoxyquinolin-4(1H)-one (I-10-f)

I-10-e (42 mg, 0.1 mmol) was dissolved in glacial acetic acid (5 ml). HBr (3 ml) was added while the solution was heated to 60° C., and the mixture was heated to 90° C. for 3 h. After the reaction was complete, the reaction mixture was poured into water, and extracted with EtOAc. The acid layer was neutralized to pH 7-8 by adding 10% NaHCO$_3$, and extracted with EtOAc (100 ml×5). The organic layer was dried over MgSO$_4$, and evaporated. The residue was recrystallized from n-hexane-EtOAc to afford I-10-f as gray solid (20.8 mg, 61.9%).

MP 152.1-152.7° C.

$^1$H-NMR (DMSO-d6, 200 MHz): δ 11.76 (1H, s, H-1), 7.67-7.74 (3H, m, H-5, H-8, H-6'), 7.46-7.49 (3H, m, H-7, H-2', H-4'), 7.27 (1H, dd, H-5'), 6.27 (1H, s, H-3), 3.80 (3H, s, OCH$_3$), 3.67 (2H, s, CH$_2$N(CH$_2$CH$_3$)$_2$), 2.53 (4H, q, J=7 Hz, CH$_2$N(CH$_2$CH$_3$)$_2$), 0.97 (6H, t, J=7 Hz, CH$_2$N(CH$_2$CH$_3$)$_2$).

Anal. calcd for C21H24N2O2: C, 74.97; H, 7.19; N, 8.33. Found: C, 74.81; H, 7.33; N, 8.31.

Anti Cancer Activities

Effects of Compounds I-1 and I-1-b on Anti-Tumor Activity In Vivo (I) Effects of Compounds I-1 and I-1-b on MCF-7 Tumor Xenograft Model I-1 Materials and Methods Female GALB/cAnN-Foxn1.E SCID mice (18-20 g; 6-8 weeks of age) were purchased from the National Animal Center and maintained in pressurized ventilated cage according to institutional regulations. The mice were implanted subcutaneously with estradiol (0.7 mg) 2 days before tumor transplantation. MCF-7 cells (2×10$^6$) were inoculated s.c. into the right flank of the mice. After appearance of a 150-mm$^3$ tumor nodule, 30 tumor-bearing mice were randomly divided into five groups for treatment with vehicle (PBS), I-1 or I-1-b. The first groups only received vehicle. The second to fifth groups were given i.p. the following treatments three times per week, respectively: I-1 (15 mg/kg), I-1 (30 mg/kg), I-1-b (22.5 mg/kg), and I-1-b (45 mg/kg). Mice were weighed and tumors were measured using calipers every week. Tumor size was calculated with the following formula: (L+W)/2, where L is the length and W is the width. On the final day of the treatment, mice were sacrificed; tumors were excised, weighted, and sectioned; and the tumor sections were embedded in OCT compound and frozen at −70° C.

I-2 Results

The effects of I-1 or I-1-b, were examined in vivo. Thirty female SCID mice were individually injected s.c. with MCF7 cells. The mice were divided into five groups (six mice per group) and treated with vehicle alone, I-1 (15 or 30 mg/kg), I-1-b (22.5 or 45 mg/kg). As shown in FIG. 1, this in vivo tumor model shows a significant reduction in tumor volume in mice treated with 45 mg/kg I-1-b when compared with control mice (P<0.001). These results demonstrate that I-1-b significantly inhibited MCF7 tumor growth in a mouse xenograft model.

(II) Effects of Compounds I-1 and I-1-b on CT-26 Intraperitoneal Tumor Model

II-1 Materials and Methods 30 male 6-week-old Balb/c mice, were purchased from the National Animal cancer and maintained in pressurized ventilated cage according to institutional regulations. CT-26 (1×10$^6$) cells were injected into peritoneal cavities at day 0. Animals were randomly assigned to anti-tumoral efficacy study (n=10). Seven days after tumor inoculation, oral administration of 5 and 10 mg/kg of I-1-b (QD for seven times) to the mice was carried out. The survival rate and body weight of the animals was monitored.

II-2 Results

II-2-1 Appearance of Mice after Treatment

Mice in the excipient control group showed overt ascites, while mice receiving orally I-1-b (5 mg/kg/day, QD×7) and I-1-b (10 mg/kg/day, QD×7) exhibited reduced ascites development.

II-2-2 the Average Life Span of Mice after Treatment

Figure 2:
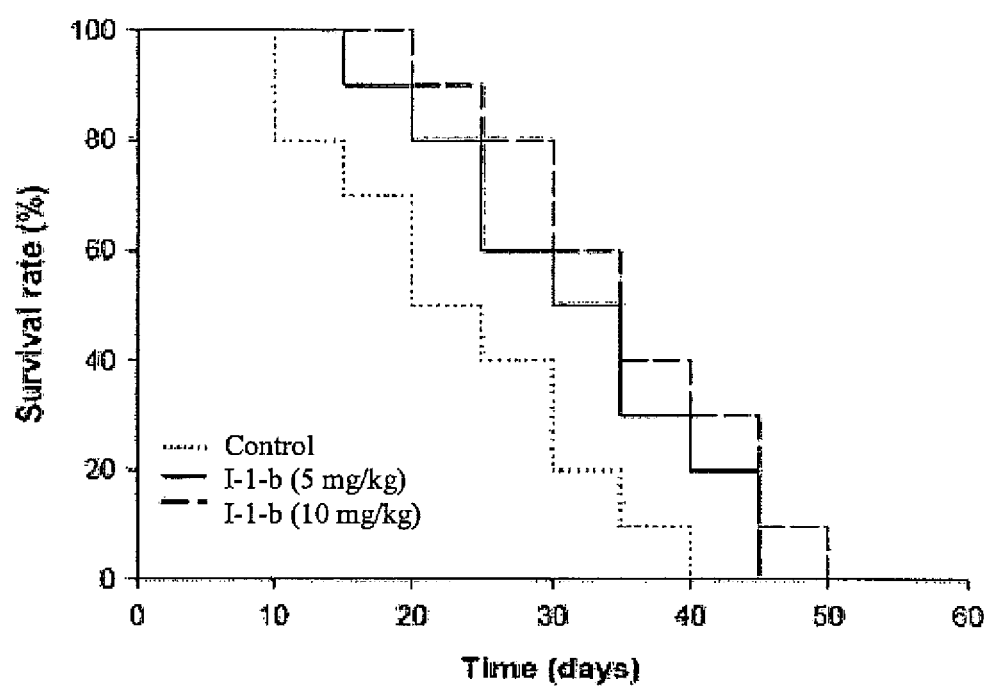
FIG. 2 shows effect of compound I-1-b on animal survival. BALB/c mice were intraperitoneally injected with CT-26 tumor cells for 7 days before beginning the treatments with compound I-1-b (5 mg/kg/day and 10 mg/kg/day QD×7).

As shown in FIG. 2, all mice in the excipient control group were dead 40 days after, while those receiving compounds I-1-b (5 mg/kg/day, QD×7) and compounds I-1-b (10 mg/kg/day, QD×7) were all dead respectively by day 45 and day 50 post challenge. The average life span was prolonged by 140% at the dose of (10 mg/kg/day, QD×7) and by 120% at the dose of (5 mg/kg/day, QD×7). A maximally tolerated dose was not achieved.

Cell Viability Assay (MTT Assay)

Cells were seeded in a 24-well microtiter plate (2×10$^4$ cells/well) overnight, then treated with DMSO (Control) or various concentrations of test compounds, and incubated for 48 hours. The effect of test compounds on cell growth was examined by the MTT (3-(4,5-dimethylthiazol-2-yl)-2,5-diphenyl tetrazolium bromide) assay. Briefly, 40 μl of MTT solution (2 mg/ml, Sigma Chemical Co.) was added to each well to make a final volume of 500 μl and incubated for 1 h at 37° C. The supernatant was aspirated, and the MTT-formazan crystals formed by metabolically viable cells were dissolved in 200 μl of DMSO. Finally, the absorbance at O.D. 550 nm was detected by enzyme-linked immunosorbent assay (ELISA) reader.

Figure 3:
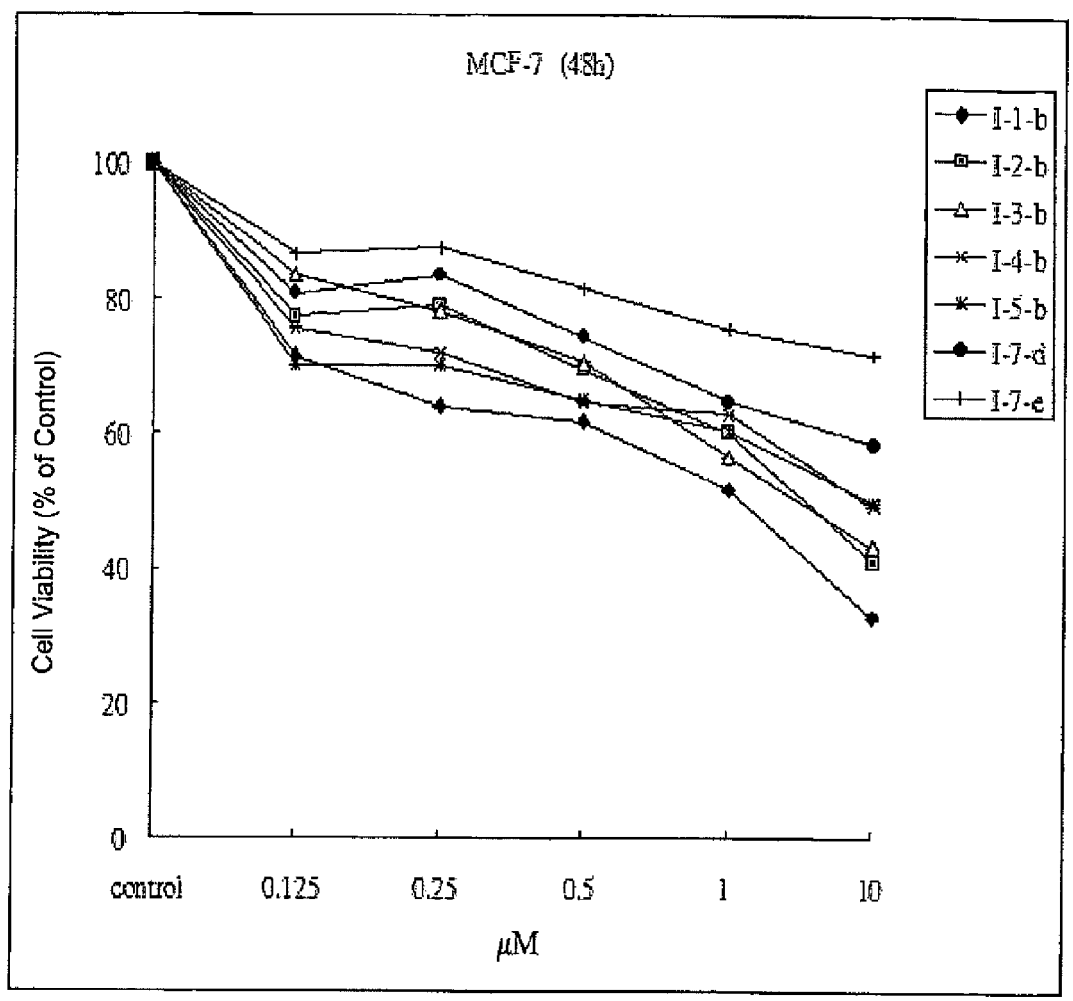
FIG. 3 shows effect of quinolone derivatives on the viability of human breast cancer cells. MCF7 cells were treated with DMSO (Control) or various concentrations (0.125 μM to 10 μM) of quinolone derivative for 48 hours and subsequent cell viability was measured by MTT assay. Results from three separate experiments were averaged and are presented as mean±standard error as shown.

Results:

Cytotoxic Effect of Compounds I-1-b, I-2-b, I-3-b, I-4-b, I-5-b, I-7-d, I-7-e Against the Human Breast Cancer MCF-7 Cells The cytotoxic effect of compounds I-1-b, I-2-b, I-3-b, I-4-b, I-5-b, I-7-d, I-7-e were evaluated in the human breast cancer MCF-7 cells. As shown in FIG. 3, treatment with 0.125 to 10 μM of these compounds caused a dose-dependent decrease of cell viability. These results indicate that compounds I-1-b, I-2-b, I-3-b, I-4-b, I-5-b, I-7-d, I-7-e show significant cytotoxicity against MCF-7 cells. Therefore, these new derivatives of 2-aryl-quinolines are proposed as potential therapeutic agents for the treatment of cancers.

Cytotoxic Activity of Compound I-7-d

In vitro cytotoxic activity of compound I-7-d was tested in HCT-116, Hep G2, NCI-H226, A549, A498 and HL-60 cells. As shown in Table 1, compound I-7-d demonstrates significant inhibition against most of the six cancer cell lines and most notably, is quite active against HCT-116 and HL-60 cells. Compound I-7-d shows an IC$_{50}$ of 0.9 μM against HCT-116 and an IC$_{50}$ of 0.5 μM against HL-60 cell. Compound I-7-d is an attractive candidate for development as a novel anti-cancer agent.

TABLE 1

| | IC$_{50}$ (μM) | | | | | |
|---|---|---|---|---|---|---|
| | HCT116 | Hep G2 | NCI-H226 | A549 | A498 | HL-60 |
| I-7-d | 0.9 | 4.1 | 4.9 | 8.1 | 2.7 | 0.5 |

* Six cancer cell lines were treated with compound I-7-d for 48 h. After treatment, cells were harvested and examined using MTT assay.
* IC$_{50}$ value means the concentration causing 50% growth-inhibitory effect.
* HCT-116, colon cancer cell line; Hep G2, hepatoma cancer cell line; NCI-H226, non-small cell lung cancer cell line; A549, lung cancer cell line; A498, renal cancer cell line; HL-60, leukemia cancer cell line.

Cytotoxic Activity of Compound I-8-e, I-9-e and I-10-f

In vitro cytotoxic activity of compound I-8-e, I-9-e and I-10-f were tested in HL-60 cells. As shown in Table 2, compound I-8-e and I-9-e demonstrated significant inhibition against HL-60 cancer cell lines. Compound I-8-e showed an IC$_{50}$ of 15 μM and compound I-9-e showed an IC$_{50}$ of 5.8 μM against HL-60 cell. Compound I-9-e is an attractive candidate for development as a novel anti-cancer agent.

TABLE 2

| Compound | IC$_{50}$ (μM) |
|---|---|
| I-8-e | 15 |
| I-9-e | 5.8 |
| I-10-f | >50 |

* HL-60 cell were treated with compound I-8-e, I-9-e and I-10-f for 48 h. After treatment, cells were harvested and examined using MTT assay.
* IC$_{50}$ value means the concentration causing 50% growth-inhibitory effect.
* HL-60, leukemia cancer cell line.

What is claimed is:

1. A phosphate derivative of 2-aryl-4-quinolone having the following formulas Ib or Ic:

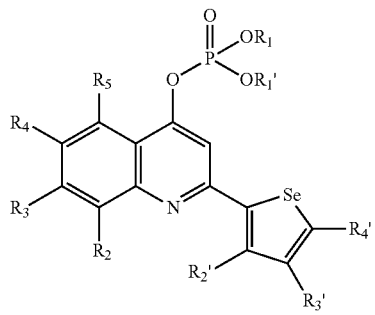

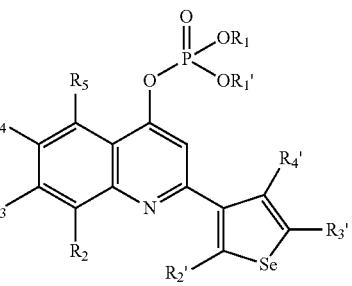

wherein

R$_2$', R$_3$', and R$_4$' independently are H, (CH$_2$)$_n$CH$_3$, Y(CH$_2$)$_n$CH$_3$, or X, wherein n is an integer of 0-4, Y is O, and X is F, Cl, or Br;

R$_2$ and R$_5$ independently are H, (CH$_2$)$_n$CH$_3$, or X, wherein n and X are defined as above;

R$_3$ and R$_4$ together is —Y(CH$_2$)$_n$Y—, wherein n and Y are defined as above; and R$_1$ and R$_1$' independently are H, Li$^+$, Na$^+$, K$^+$, N$^+$R$_8$R$_9$R$_{10}$R$_{11}$ or benzyl wherein R$_8$, R$_9$, R$_{10}$ and R$_{11}$ independently are H, (CH$_2$)$_n$YH, (CH$_2$)$_n$N(C$_n$H$_{2n+1}$)(C$_m$H$_{2m+1}$) or (CH$_2$)$_n$CH$_3$, wherein n and Y are defined as above, and m is an integer of 0-4.

2. The phosphate derivative according to claim 1, wherein R$_2$', R$_3$' and R$_4$' are all H; or one of R$_2$', R$_3$' and R$_4$' is F or OCH$_3$, and the others thereof are H.

3. The phosphate derivative according to claim 1, wherein R$_1$ and R$_1$' are benzyl.

4. The phosphate derivative according to claim 3, wherein R$_2$', R$_3$', R$_4$', R$_2$ and R$_5$ are all H, and R$_3$ and R$_4$ together is —O(CH$_2$)O—.

5. A pharmaceutical composition for the killing of solid cancer cells, which comprises a therapeutically effective amount of a phosphate derivative of 2-aryl-4-quinolone as set forth in claim 1 or a pharmaceutically acceptable salt thereof, as an active ingredient, in admixture with a pharmaceutically acceptable carrier or diluent for the active ingredient, wherein the solid cancer cells comprise human breast cancer, wherein R$_2$', R$_3$', R$_4$', R$_2$ and R$_5$ are all H, and R$_3$ and R$_4$ together is —O(CH$_2$)O—.

* * * * *